United States Patent
Oberdorf et al.

[11] Patent Number: 6,034,131
[45] Date of Patent: Mar. 7, 2000

[54] DIPHENYLETHERS, PROCESS AND INTERMEDIATE PRODUCTS FOR THEIR PREPARATION, AND THEIR USE

[75] Inventors: Klaus Oberdorf, Heidelberg; Wassilios Grammenos, Ludwigshafen; Hubert Sauter, Mannheim; Thomas Grote, Schifferstadt; Bernd Müller, Frankenthal; Reinhard Kirstgen, Nuestadt; Herbert Bayer, Mannheim; Arne Ptock, Ludwigshafen; Michael Rack, Heidelberg; Albrecht Harreus, Ludwigshafen; Franz Röhl, Schifferstadt; Eberhard Ammermann, Heppenheim; Volker Harries, Frankenthal; Gisela Lorenz, Hambach; Siegfried Strathmann, Limburgerhof, all of Germany

[73] Assignee: BASF Aktiengesellschaft, Ludwigshafen, Germany

[21] Appl. No.: 09/142,200
[22] PCT Filed: Mar. 4, 1997
[86] PCT No.: PCT/EP97/01079
  § 371 Date: Sep. 3, 1998
  § 102(e) Date: Sep. 3, 1998
[87] PCT Pub. No.: WO97/32842
  PCT Pub. Date: Sep. 12, 1997

[30] Foreign Application Priority Data

Mar. 8, 1996 [DE] Germany ............ 196 09 037
Mar. 13, 1996 [DE] Germany ............ 196 09 768

[51] Int. Cl.[7] ............ C07C 229/28; C07C 251/38; C07C 251/52; A01N 37/16
[52] U.S. Cl. ............ 514/559; 560/27; 560/35; 564/147; 564/163; 514/619
[58] Field of Search ............ 560/35, 27; 564/147, 564/163; 514/559, 619

[56] References Cited

U.S. PATENT DOCUMENTS 5,298,527 3/1994 Grammenos et al. .
5,416,068 5/1995 Grammenos et al. .

FOREIGN PATENT DOCUMENTS

| 307 103 | 3/1989 | European Pat. Off. . |
| 398 692 | 11/1990 | European Pat. Off. ...... C07C 251/40 |
| 0513 580 | 11/1992 | European Pat. Off. ...... C07D 261/20 |
| 0673 923 | 9/1995 | European Pat. Off. ...... C07C 251/38 |
| 93/15046 | 8/1993 | WIPO . |

OTHER PUBLICATIONS

Chem. Absts., vol. 60, No. 9, No. 10731a.

*Primary Examiner*—Gary Geist
*Assistant Examiner*—Brian J. Davis
*Attorney, Agent, or Firm*—Keil & Weinkauf

[57] ABSTRACT

A diphenyl ether of the formula I,

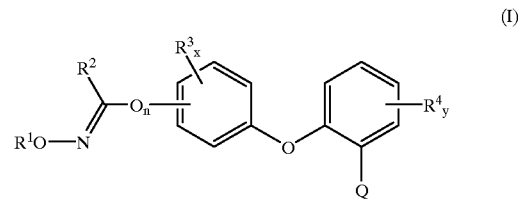

or a salt or N-oxide thereof wherein

Q is $C(CO_2CH_3)=CHCH_3$, $C(CONH_2)=CHOCH_3$, $C(CO_2CH_3)=NOCH_3$, $C(CONHCH_3)=NOCH_3$ or $N(OCH_3)-CO_2CH_3$;

n is 0 or 1;

$R^1$ is hydrogen or a carbon bonded organic radical;

$R^2$ is hydrogen or an organic radical bonded via C, O, S or N;

x is 0, 1 or 2;

$R^3$ is cyano, nitro, halogen or an organic radical bonded via C, O, S or N; or y is 0, 1, 2 or 3;

$R^4$ is cyano, halogen, alkyl, haloalkyl or alkoxy, intermediates and processes for its preparation, and its use.

20 Claims, No Drawings

DIPHENYLETHERS, PROCESS AND INTERMEDIATE PRODUCTS FOR THEIR PREPARATION, AND THEIR USE

TECHNICAL FIELD

The present invention relates to diphenyl ethers of the formula I,

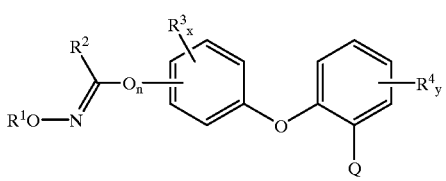

and to their salts and N-oxides where the substituents and indices have the following meanings:

Q is $C(CO_2CH_3)=CHCH_3$, $C(CO_2CH_3)=CHOCH_3$, $C(CONH_2)=CHOCH_3$, $C(CO_2CH_3)=NOCH_3$, $C(CONHCH_3)=NOCH_3$ or $N(OCH_3)-CO_2CH_3$;

n is 0 or 1;

$R^1$ is hydrogen or
an organic radical linked via a carbon atom;

$R^2$ is hydrogen, cyano, halogen or
an organic radical linked via a carbon, oxygen, sulfur or nitrogen atom, or
in the event that n is 1, an organic radical linked via a carbon atom;

x is 0, 1 or 2, it being possible for the radicals $R^3$ to be different if x is 2;

$R^3$ is cyano, nitro, halogen or
an organic radical linked via a carbon, oxygen, sulfur or nitrogen atom or $R^2$ and a substituent $R^3$ which is adjacent to the group $O_n-C(R^2)=NOR^1$ is $C_2-C_3$-alkylene which can be interrupted by an oxygen or sulfur atom or can be linked to the phenyl ring via an oxygen or sulfur atom;

y is 0, 1, 2 or 3, it being possible for the radicals $R^4$ to be different if y is 2 or 3;

$R^4$ is cyano, halogen, $C_1-C_4$-alkyl, $C_1-C_4$-haloalkyl or $C_1-C_4$-alkoxy.

The invention furthermore relates to processes and intermediates for the preparation of these compounds and to their use for controlling animal pests and harmful fungi.

BACKGROUND ART

The literature (EP-A 253 213; EP-A 254 426; EP-A 280 185; EP-A 307 103; EP-A 398 692; EP-A 477 631; EP-A 513 580; WO-A 93/15,046) discloses phenyl ethers which have fungicidal, or fungicidal and insecticidal, properties which differ from the compounds according to the invention by their substituents.

It is an object of the present invention to provide compounds with an improved activity and a widened spectrum of action.

DISCLOSURE OF INVENTION

We have found that this object is achieved by the compounds I as defined at the outset. We have furthermore found processes and intermediates for the preparation of these compounds and their use for controlling animal pests and harmful fungi.

Compounds I are accessible via various routes by processes known per se from the literature.

For example, the construction of the group Q is disclosed in the literature cited at the outset and is carried out in general and in particular following the processes described therein.

When synthesizing the compounds I where n is 0, a procedure is usually used in which a phenol of the formula IIa is converted with a halobenzene of the formula IIIa in an inert solvent to give the corresponding ether of the formula IVa and IVa is subsequently reacted with an O-substituted hydroxylamine ($R^1-O-NH_2$) or with a salt thereof to give I.

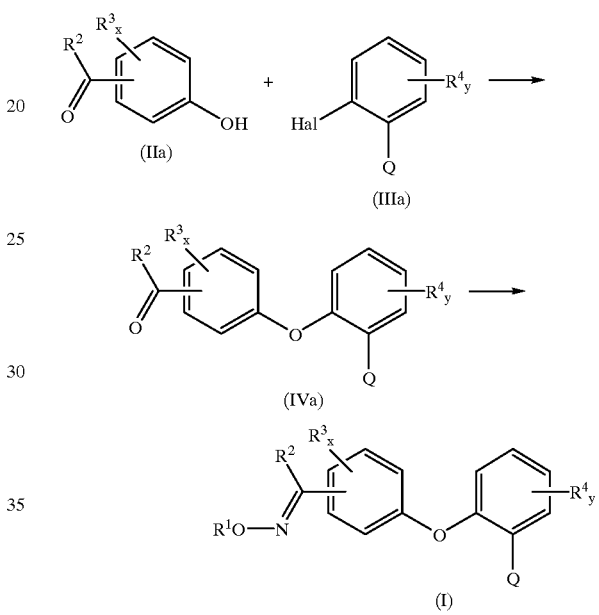

Hal in the formula IIIa is a halogen atom, such as fluorine, chlorine, bromine and iodine, preferably fluorine, chlorine or bromine.

1a) The reaction of IIa with IIIa is usually carried out in an inert solvent at from 0° C. to 130° C., preferably 20° C. to 80° C., in the presence of a base.

Suitable solvents are aliphatic hydrocarbons, such as pentane, hexane, cyclohexane and petroleum ether, aromatic hydrocarbons such as toluene, o-, m- and p-xylene, ethers, such as diethyl ether, diisopropyl ether, tert-butyl methyl ether, dioxane, anisole and tetrahydrofuran, nitrites, such as acetonitrile and propionitrile, ketones such as acetone, methyl ethyl ketone, diethyl ketone and tert-butyl methyl ketone, as well as dimethyl sulfoxide and dimethylformamide, especially preferably tetrahydrofuran, acetonitrile, dimethyl sulfoxide and acetone. Mixtures of these can also be used.

Suitable bases are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and alkali metal hydrogen carbonates, such as sodium hydrogen carbonate, organometal compounds, in particular alkali metal alkyls, such as methyllithium, butyllithium and phenyllithium, alkylmagnesium halides, such as methylmagnesium chloride, and alkali metal alkoxides and alkaline earth metal alkoxides, such as sodium methoxide, sodium ethoxide, potassium ethoxide, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, or else bicyclic amines. Potassium carbonate, sodium hydride and potassium tert-butylate are especially preferred. In general, the bases are employed in catalytic amounts, but they can also be used in equimolar amounts, in an excess or, if desired, as the solvent.

The starting materials are generally reacted with each other in equimolar amounts. It may be advantageous for the yield to employ an excess of IIa based on IIIa.

1b) The reaction of IVa with the O-substituted hydroxylamine or a salt thereof is usually carried out in an inert solvent at from 0° C. to 80° C., preferably 20° C. to 60° C., in the presence or absence of an acid or in the presence or absence of a base if the O-substituted hydroxylamine is liberated from its salt.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, alcohols, such as methanol, ethanol, n-propanol, isopropanol, n-butanol and tert-butanol, or else dimethyl sulfoxide, dimethylformamide and pyridine, especially preferably methanol and pyridine. Mixtures of these can also be used.

Suitable bases are, generally, inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and alkali metal hydrogen carbonates, such as sodium hydrogen carbonate, organometal compounds, in particular alkali metal alkyls, such as methyllithium, butyllithium and phenyllithium, alkylmagnesium halides, such as methylmagnesium chloride, and alkali metal alkoxides and alkaline earth metal alkoxides, such as sodium methoxide, sodium ethoxide, potassium ethoxide, potassium tert-butanolate and dimethoxymagnesium, moreover organic bases, eg. tertiary amines, such as trimethylamine, triethylamine, triisopropylethylamine and N-methylpiperidine, pyridine, substituted pyridines, such as collidine, lutidine and 4-dimethylaminopyridine, or else bicyclic amines. Pyridine and sodium hydroxide are especially preferred. In general, the bases are employed in catalytic amounts, but they can also be used in equimolar amounts, in an excess or, if desired, as the solvent.

Acids and acidic catalysts which are used are inorganic acids, such as hydrofluoric acid, hydrochloric acid, hydrobromic acid, sulfuric acid and perchloric acid, Lewis acids, such as borontrifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid. The acids are generally employed in catalytic amounts.

In general, the starting materials are reacted with each other in equimolar amounts. It may be advantageous for the yield to employ the hydroxyl amine or its salt in an excess based on IVa.

Similarly, the compounds I where n is 0 are obtained by first converting a phenol of the formula IIa with an O-substituted hydroxylamine ($R^1$—O—$NH_2$) or with a salt thereof to give the corresponding compound of the formula IIb and subsequently reacting IIb with a halobenzene of the formula IIIa in an inert solvent to give I.

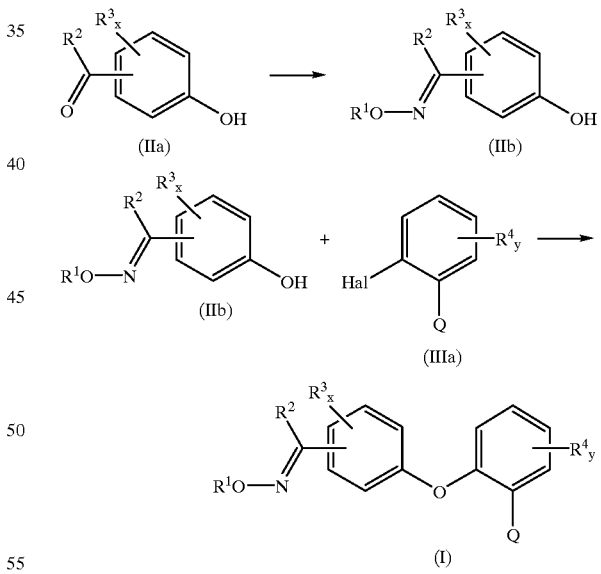

In general and in particular, the reactions are carried out by the methods described above.

The starting materials of the formula IIa where n is 0 can be obtained by reacting a suitably substituted phenol of the formula IIc with an activated carboxylic acid of the formula va in an inert solvent in the presence of an organometallic base [cf. J. Organomet. Chem. 56 (1973), 53–66; Chem. Ber. 125 (1992), 1169–1190].

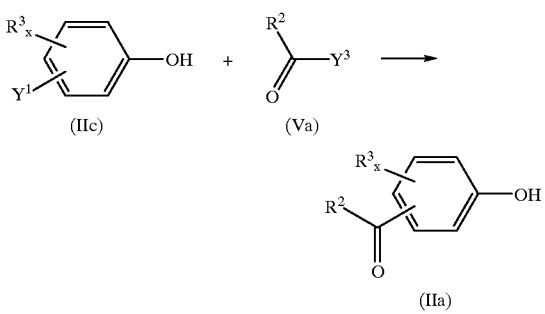

$Y^1$ in formula IIc is a halogen atom, eg. fluorine, chlorine, bromine and iodine, especially bromine and iodine.

$Y^3$ in formula Va is a halogen atom, eg. fluorine, chlorine, bromine and iodine, especially chlorine, or an amide or ester radical. It is also possible to employ a corresponding cyanide $R^2$—C≡N in place of the compound Va.

This reaction is usually carried out in an inert solvent in the presence of an organometallic base at from −75° C. to 40° C., preferably −75° C. to 0° C.

Suitable solvents are aliphatic hydrocarbons, such as pentane, hexane, cyclohexane and petroleum ether, aromatic hydrocarbons, such as toluene, o-, m- and p-xylene, ethers, such as diethyl ether, diisopropyl ether, tert-butyl methyl ether, dioxane, anisole and tetrahydrofuran, or else dimethyl sulfoxide and dimethylformamide, especially preferably diethyl ether and tetrahydrofuran. Mixtures of these can also be used.

Organometallic bases which are generally suitable are organometallic compounds, in particular alkali metal alkyls, such as methyllithium, butyllithium and phenyllithium, alkylmagnesium halides, such as methylmagnesium chloride. n-Butyllithium is especially preferred. The bases can generally be used in equimolar amounts or in an excess.

In general, the starting materials are reacted with each other in equimolar amounts. It may be advantageous for the yield to employ Va in an excess based on IIc.

In a further method, the compounds IIa are also obtained by reacting a hydroxybenzoyl halide of the general formula IId with an organometallic compound ($R^2$—M; M is the equivalent of a metal ion) in an inert solvent [cf. DE-A 38 38 243; EP-A 446 872].

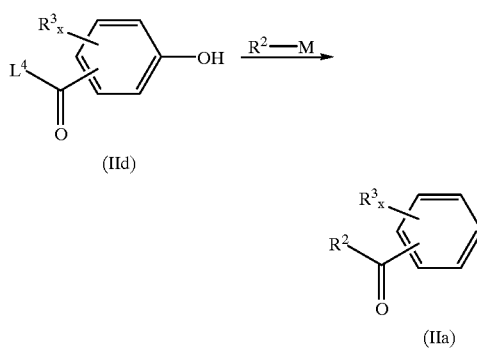

Especially suitable metals are lithium, magnesium, copper and zinc.

$L^4$ in formula IId is a halogen atom, eg. fluorine, chlorine, bromine and iodine, especially chlorine.

This reaction is normally carried out in an inert solvent at from −80° C. to 20° C., preferably −75° C. to 0° C.

Suitable solvents are aliphatic hydrocarbons, such as pentane, hexane, cyclohexane and petroleum ether, aromatic hydrocarbons, such as toluene, o-, m- and p-xylene, ethers, such as diethyl ether, diisopropyl ether, tert-butyl methyl ether, dioxane, anisole and tetrahydrofuran, especially preferably diethyl ether and tetrahydrofuran. Mixtures of these can also be used.

In general, the starting materials are reacted with each other in equimolar amounts. It may be advantageous for the yield to employ the organometallic compound in an excess based on IId.

The starting materials of the formula IIa are furthermore also obtained by converting a suitably substituted phenol of the formula IIe with an alkyl halide (R'—Hal; R' is $C_1$–$C_4$-alkyl, Hal is a halogen atom, such as fluorine, chlorine, bromine and iodine, preferably chlorine and bromine) in the presence of a base to give the corresponding alkyl phenyl ether of the formula IIf, subsequently converting IIf by a method similar to the process described above (reaction of IIc) into the corresponding ether IIg by reacting it with an activated carboxylic acid of the formula Va and subsequently cleaving IIg to give IIa.

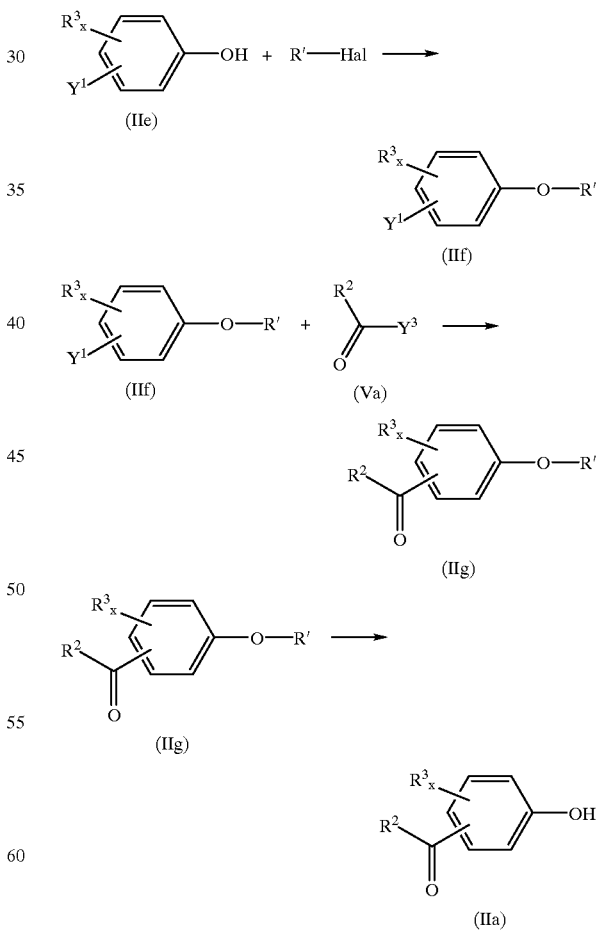

a) The etherification of IIe to IIf is usually carried out at from 0° C. to 120° C., preferably 20° C. to 80° C., in the presence of an inert solvent.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, The intermediates of the formula IVa can furthermore be obtained by reacting an ether of the formula IVb either a) with an activated carboxylic acid of the formula Va in the presence of an organometallic base in an inert solvent or b) with an organotin compound of the formula VI in an inert solvent.

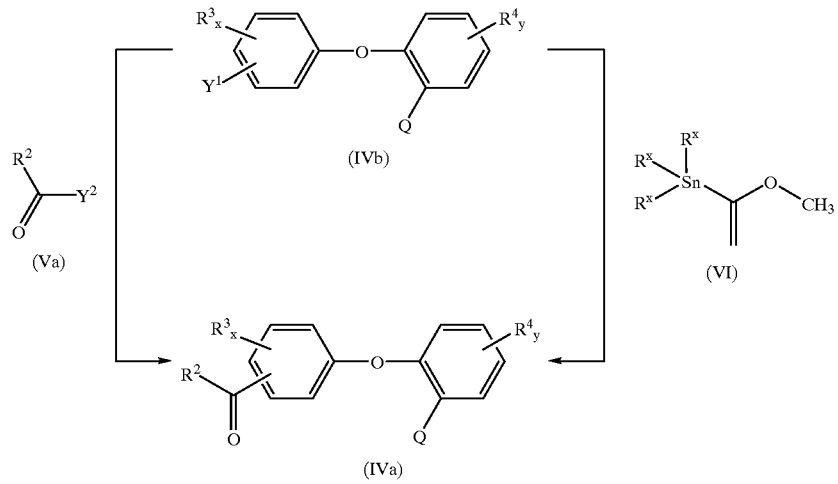

diethyl ketone and tert-butyl methyl ketone, or else dimethyl sulfoxide and dimethylformamide, especially preferably dimethylformamide. Mixtures of these can also be used.

The phenol IIe and the alkyl halide are generally reacted with each other in equimolar amounts. It may be advantageous for the yield to employ the alkyl halide in an excess based on IIe, or as the solvent.

b) The reaction of the ether IIf with the activated carboxylic acid Va is generally and in particular carried out under the conditions described for the preparation of the compounds IIa from the compounds IIc.

c) The ether cleavage of IIg to IIa is usually carried out in an inert solvent at from 0° C. to 130° C., preferably 60° C. to 100° C., in the presence of an acid.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, nitriles, such as acetonitrile and propionitrile, alcohols, such as methanol, ethanol, n-propanol, isopropanol, n-butanol and tert-butanol, or else dimethyl sulfoxide and dimethylformamide, especially preferably methylene chloride. Mixtures of these can also be used.

Suitable acids and acidic catalysts are inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid. The acids are generally employed in catalytic amounts, but they can also be used in equimolar amounts, in an excess or, if desired, as the solvent.

$Y^1$ in formula IVb is a halogen atom, such as fluorine, chlorine, bromine and iodine, in particular bromine and iodine.

$Y^2$ in formula Va is a halogen atom, such as fluorine, chlorine, bromine and iodine, in particular chlorine.

The radicals Rx in formula VI are independent of one another and are alkyl.

a) The reaction of the ether IVb with the activated carboxylic acid Va is carried out in general and in particular under the conditions described for the preparation of the compounds IIa from the compounds IIc.

b) The reaction of the ether IVb with the organotin compound VI is usually carried out in an inert solvent at from −70° C. to 40° C., preferably −70° C. to 0° C., in the presence of a catalyst such as $Pd[P(C_6H_5)_3]_3$ and $PdCl_2$.

Suitable solvents are aliphatic hydrocarbons, such as pentane, hexane, cyclohexane and petroleum ether, aromatic hydrocarbons, such as toluene, o-, m- and p-xylene, ethers, such as diethyl ether, diisopropyl ether, tert-butyl methylether, dioxane, anisole and tetrahydrofuran, nitriles such as acetonitrile and propionitrile, or else dimethyl sulfoxide and dimethylformamide, especially preferably tetrahydrofuran and diethylether. Mixtures of these can also be used.

The educts are generally reacted with each other in equimolar amounts. It may be advantageous for the yield to employ the organotin compound VI in an excess based on the ether IVb.

Compounds of the formula I where n is 1 are preferably obtained by converting a diphenyl ether of the formula IVc with a cyanide $R^2$—C≡N in an inert solvent in the presence of hydrochloric acid to give the chlorohydroxamate VIIc and subsequently reacting VIIc with an O-substituted hydroxylamide ($R^1$—$ONH_2$) or a salt thereof to give I.

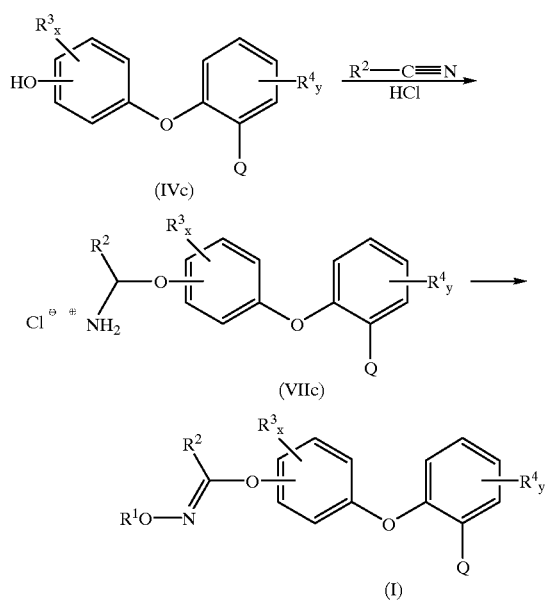

The reaction to give the chlorohydroxamate VIIc is carried out in general and in particular under the conditions described in U.S. Pat. No. 4,743,701.

The reaction of VIIc to I proceeds in general and in particular in accordance with the conditions described above for the reaction of IIa to IIb.

In an especially preferred process, the compounds I where n is 0 and Q is $C(CO_2CH_3)=NOCH_3$ are obtained by converting a phenol of the formula IIa with a halobenzene of the formula IIIb in an inert solvent to give the corresponding ether of the formula VIIa, subsequently reacting VIIa with an O-substituted hydroxylamine ($R^1-ONH_2$) or a salt thereof to give VIIb and reacting VIIb with O-methylhydroxylamine ($CH_3-ONH_2$) or with a salt thereof.

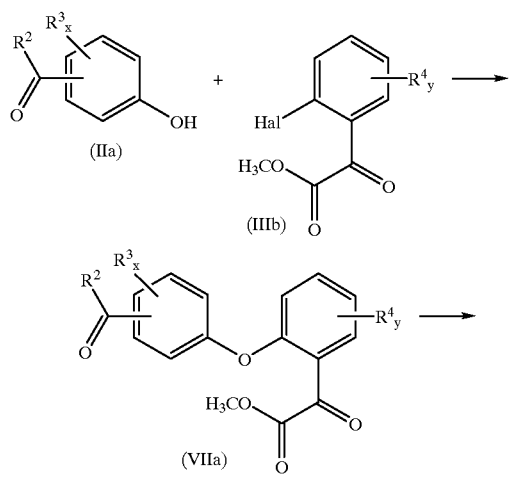

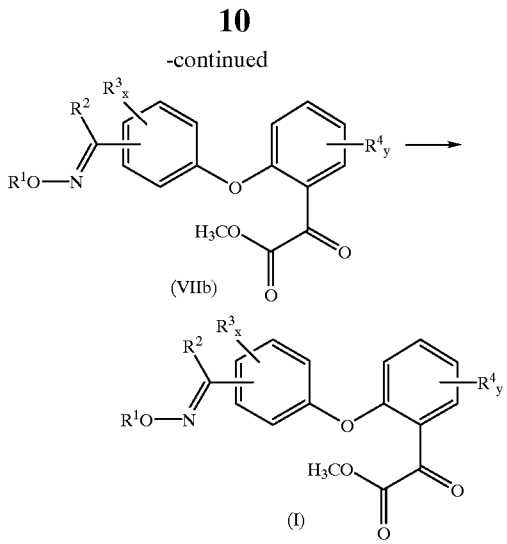

The reaction of IIa with IIIb is carried out in accordance with the conditions described above for the reaction of IIb with IIIa.

The reaction of VIIa to VIIb is carried out in accordance with the conditions described above for the reaction of IIa to IIb.

The reaction of VIIb to I is carried out in accordance with the conditions described above for the reaction of IIa to IIb.

In an especially preferred process, the compounds VIIb can also be obtained by reacting a compound of the formula IIb with a halobenzene of the formula IIIb.

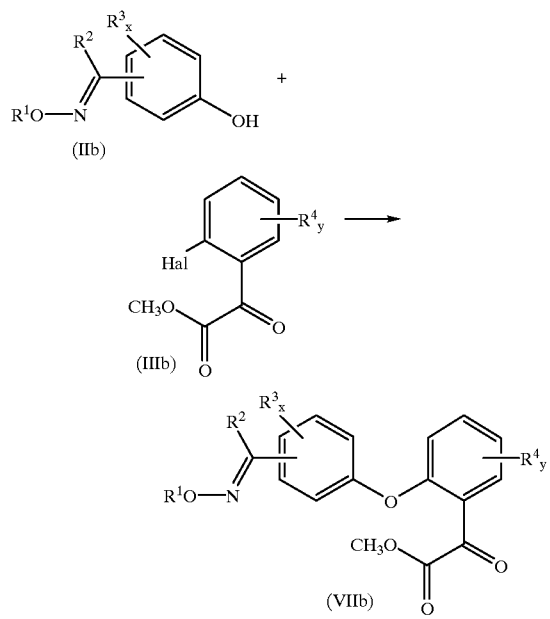

The reaction is carried out in general and in particular in accordance with the conditions described above.

In a similar manner, the compounds of the formula I where n is 0 and Q is $C(CONHCH_3)=NOCH_3$ are especially preferably obtained by first converting a compound of the formula IIb with a halobenzene of the formula IIIc in an inert solvent to give the corresponding ether of the formula VIId and reacting VIId with O-methylhydroxylamine (CH$_3$O—NH$_2$) or the salt thereof.

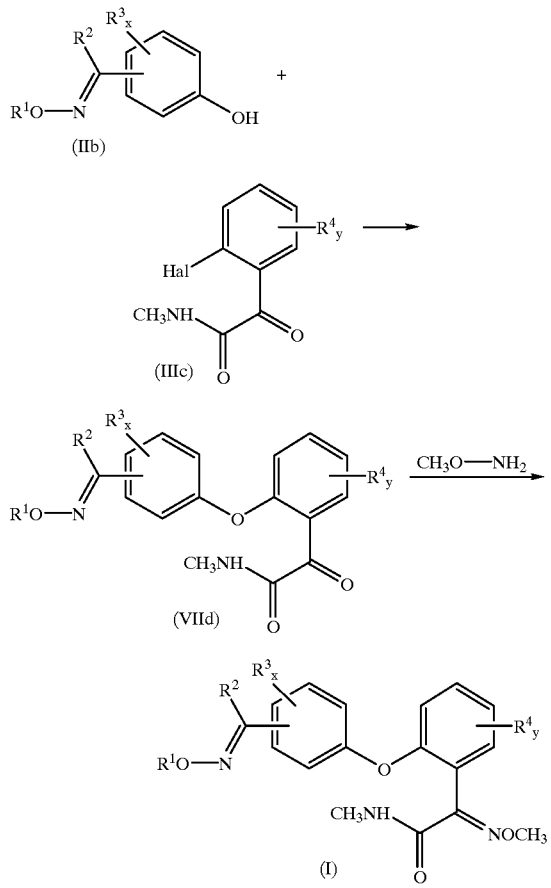

Hal in formula IIIc is a halogen atom, in particular fluorine.

In a further process, compounds I where Q is C(CO$_2$CH$_3$)=CHOCH$_3$ are preferably obtained by converting a phenylacetic acid of the formula VIIIa in a manner known per se in an inert solvent to give the corresponding β-hydroxyacrylate VIIIb and reacting VIIIb with a methylating reagent to give I.

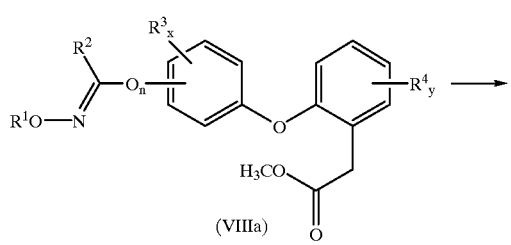

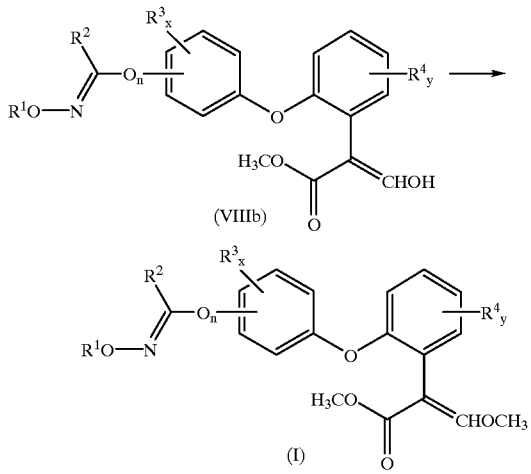

The reaction of the phenylacetic acid derivatives VIIIa with 30 methyl formate is usually carried out at from −20° C. to 60° C., preferably 10° C. to 50° C.

Suitable solvents are methyl formate itself, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethylether, diisopropyl ether, tert-butyl methyl ether, dioxane, anisole and tetrahydrofuran, nitrites, such as acetonitrile and propionitrile, alcohols, such as methanol, ethanol, n-propanol, isopropanol, n-butanol and tert-butanol, or else dimethyl sulfoxide and dimethylformamide, especially preferably methanol, tetrahydrofuran, dimethyl sulfoxide and dimethylformamide.

Mixtures of these can also be used.

Bases which are generally used are inorganic compounds such as alkali metal hydrides and alkaline earth metal hydrides, such as lithium hydride, sodium hydride, potassium hydride and calcium hydride, alkali metal amides, such as lithium diisopropyl amide, lithium amide, sodium amide and potassium amide, organometallic compounds, in particular alkali metal alkyls, such as methyllithium, n-butyllithium and phenyllithium, alkylmagnesium halides, such as methylmagnesium chloride, or else alkali metal alkoxides and alkaline earth metal alkoxides, such as sodium methoxide, sodium ethoxide, potassium ethoxide, potassium tert-butanolate and dimethoxymagnesium.

Especially preferred substances are lithium diisopropylamide, sodium hydride, n-butyllithium, sodium methoxide and potassium tert-butanolate.

In general, the bases are employed in equimolar amounts or in an excess.

In general, the starting materials are reacted with each other in equimolar amounts. It may be advantageous for the yield to employ the methyl formate in an excess based on VIIIa.

The methylation of beta-hydroxyacrylates VIIIb is normally carried out at from 0° C. to 60° C., preferably 0° C. to 30° C.

Examples of reagents which are suitable for transferring the methyl group are methyl chloride, methyl bromide, methyl iodide or dimethyl sulfate, in particular methyl iodide and dimethyl sulfate.

Solvents which are used are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide and dimethylformamide.

Mixtures of these can also be used.

Bases which are generally suitable are inorganic compounds such as alkali metal hydroxides and alkaline earth metal hydroxides, such as lithium hydroxide, sodium hydroxide, potassium hydroxide, calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal carbonates and alkaline earth metal carbonates, such as sodium carbonate, potassium carbonate, magnesium carbonate and calcium carbonate, or else alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, or else alkali metal alkoxides and alkaline earth metal alkoxides, such as sodium methoxide, sodium ethoxide, potassium ethoxide, potassium tert-butanolate and dimethoxymagnesium, moreover organic bases, eg. tertiary amines, such as trimethylamine, triethylamine, diisopropylethylamine and N-methylpiperidine, pyridine, substituted pyridines, such as collidine, lutidine and 4-dimethylaminopyridine, or else bicyclic amines.

Especially preferred substances are sodium carbonate, potassium carbonate, sodium hydrogen carbonate and sodium methoxide.

In general, the bases are used in equimolar amounts, in an excess or, if desired, as the solvent.

In general, the methylating agent is employed in equimolar amounts based on VIIIb.

The reaction mixtures are worked up in the customary manner, eg. by mixing with water, phase separation and, if desired, chromatographic purification of the crude products. Some of the intermediates and end products are obtained in the form of colorless or pale brown viscous oils which are freed or purified from volatile components under reduced pressure and at moderately elevated temperatures. If the intermediates and end products are obtained in the form of solids, they may also be purified by recrystallization or digestion.

Intermediates which are especially suitable for the preparation of the compounds I where n is 0 are those of the general formula IV

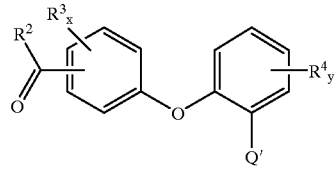
(IV)

where $R^2$, $R^3$, $R^4$, x and y have the abovementioned meanings and Q' is one of the following groups:
$CH_2$—$CO_2CH_3$, $C(O)$—$CO_2CH_3$ or a radical Q.

Intermediates which are furthermore preferred for the preparation of the compounds I are those of the general formula IV',

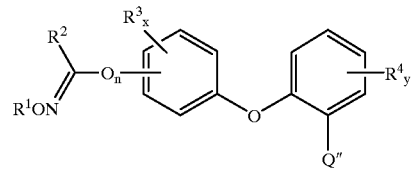
(IV')

where $R^1$, $R^2$, $R^3$, $R^4$, n, x and y have the abovementioned meanings and Q" is one of the following groups: $CH_2$—$CO_2CH_3$, $C(O)$—$CO_2CH_3$ or $C(CO_2CH_3)$=$CHOH$.

Due to their C=C and C=N double bonds, the compounds I can be obtained from the preparation in the form of E/Z isomer mixtures, which can be separated into individual compounds in the customary manner, eg. by crystallization or chromatography.

If the synthesis yields isomer mixtures, a separation is, however, in general not necessarily required since some of the individual isomers can be converted into each other during formulation for use or upon use (eg. when exposed to light, acids or bases). Similar conversions can also take place after use, for example in the case of the treatment of plants in the treated plant or in the harmful fungus or animal pest to be controlled.

As regards the C=$NOR^1$ double bond, the E isomers of the compounds I are preferred with a view to their activity (configuration based on the $R^2$ group relative to the $OR^1$ group)

In the definitions of the symbols given in the formulae above, collective terms were used which generally represent the following substituents:

Halogen: fluorine, chlorine, bromine and iodine;

Alkyl: saturated, straight-chain or branched hydrocarbon radicals having 1 to 4, 6, 8 or 10 carbon atoms, eg. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 10 carbon atoms (as mentioned above), it being possible for some or all of the hydrogen atoms in these groups to be replaced by halogen atoms as mentioned above, eg. $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 10 carbon atoms (as mentioned above) which are linked to the skeleton via an oxygen atom (—O—);

Haloalkoxy: straight-chain or branched haloalkyl groups having 1 to 10 carbon atoms (as mentioned above) which are linked to the skeleton via an oxygen atom (—O—);

Alkylthio: straight-chain or branched alkyl groups having 1 to 10 or 1 to 4 carbon atoms (as mentioned above) which are linked to the skeleton via a sulfur atom (—S—);

Alkylamino: a straight-chain or branched alkyl group having 1 to 10 carbon atoms (as mentioned above) which is linked to the skeleton via an amino group (—NH—);

Dialkylamino: two straight-chain or branched alkyl groups, independent of each other, having in each case 1 to 10 carbon atoms (as mentioned above) which are linked to the skeleton via a nitrogen atom;

Alkylcarbonyl: a straight-chain or branched alkyl group having 1 to 10 carbon atoms (as mentioned above) which is linked to the skeleton via a carbonyl group (—CO—);

Alkoxycarbonyl: an alkoxy group having 1 to 10 carbon atoms (as mentioned above) which is linked to the skeleton via a carbonyl group (—CO—);

Alkylthiocarbonyl: an alkylthio group having 1 to 10 carbon atoms (as mentioned above) which is linked to the skeleton via a carbonyl group (—CO—);

Alkylaminocarbonyl: an alkylamino group having 1 to 10 carbon atoms (as mentioned above) which is linked to the skeleton via a carbonyl group (—CO—);

Dialkylaminocarbonyl: a dialkylamino group (as mentioned above) which is linked to the skeleton via a carbonyl group (—CO—);

Alkylcarbonyloxy: a straight-chain or branched alkyl group having 1 to 10 carbon atoms (as mentioned above) which is linked to the skeleton via a carbonyloxy group (—$CO_2$—);

Alkylcarbonylthio: a straight-chain or branched alkyl group having 1 to 10 carbon atoms (as mentioned above) which is linked to the skeleton via a carbonylthio group (—COS—);

Alkylcarbonylamino: a straight-chain or branched alkyl group having 1 to 10 carbon atoms (as mentioned above) which is linked to the skeleton via a carbonylamino group (—CONH—);

Alkylsulfonyl: a straight-chain or branched alkyl group having 1 to 10 carbon atoms (as mentioned above) which is linked to the skeleton via a sulfonyl group (—$SO_2$—);

Alkoxysulfonyl: an alkoxy group having 1 to 10 carbon atoms (as mentioned above) which is linked to the skeleton via a sulfonyl group (—$SO_2$—);

Alkylthiosulfonyl: an alkylthio group having 1 to 10 carbon atoms (as mentioned above) which is linked to the skeleton via a sulfonyl group (—$SO_2$—);

Alkylaminosulfonyl: an alkylamino group having 1 to 10 carbon atoms (as mentioned above) which is linked to the skeleton via a sulfonyl group (—$SO_2$—);

Dialkylaminosulfonyl: a dialkylamino group (as mentioned above) which is linked to the skeleton via a sulfonyl group (—$SO_2$—);

Alkenyl: unsaturated straight-chain or branched hydrocarbon radicals having 2 to 4, 6, 8 or 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated straight-chain or branched hydrocarbon radicals having 2 to 10 carbon atoms and a double bond in any position (as mentioned above), it being possible for some or all of the hydrogen atoms in these groups to be replaced by halogen atoms as mentioned above, in particular fluorine, chlorine and bromine;

Alkenyloxy: unsaturated straight-chain or branched hydrocarbon radicals having 3 to 10 carbon atoms and a double bond in any position which is not adjacent to the hetero atom (as mentioned above) which are linked to the skeleton via an oxygen atom (—O—);

Haloalkenyloxy: unsaturated straight-chain or branched alkenyloxy groups having 3 to 10 carbon atoms (as mentioned above), it being possible for some or all of the hydrogen atoms in these groups to be replaced by halogen atoms as mentioned above, in particular fluorine, chlorine and bromine;

Alkenylthio: unsaturated straight-chain or branched hydrocarbon radicals having 3 to 10 carbon atoms and a double bond in any position which is not adjacent to the hetero atom (as mentioned above) which are linked to the skeleton via a sulfur atom (—S—);

Alkenylamino: unsaturated straight-chain or branched hydrocarbon radicals having 3 to 10 carbon atoms and a double bond in any position which is not adjacent to the hetero atom (as mentioned above) which are linked to the skeleton via an amino group (—NH—);

Alkenylcarbonyl: unsaturated straight-chain or branched hydrocarbon radicals having 2 to 10 carbon atoms and a double bond in any position (as mentioned above) which are linked to the skeleton via a carbonyl group (—CO—);

Alkenyloxycarbonyl: straight-chain or branched alkenyloxy groups having 3 to 10 carbon atoms (as mentioned above) which are linked to the skeleton via a carbonyl group (—CO—);

Alkenylthiocarbonyl: straight-chain or branched alkenylthio groups having 3 to 10 carbon atoms (as mentioned above) which are linked to the skeleton via a carbonyl group (—CO—);

Alkenylaminocarbonyl: straight-chain or branched alkenylamino groups having 3 to 10 carbon atoms (as mentioned above) which are linked to the skeleton via a carbonyl group (—CO—);

Alkenylcarbonyloxy: unsaturated straight-chain or branched hydrocarbon radicals having 2 to 10 carbon atoms and a double bond in any position (as mentioned above) which are linked to the skeleton via a carbonyloxy group (—CO$_2$—);

Alkenylcarbonylthio: unsaturated straight-chain or branched hydrocarbon radicals having 2 to 10 carbon atoms and a double bond in any position (as mentioned above) which are linked to the skeleton via a carbonylthio group (—COS—);

Alkenylcarbonylamino: unsaturated straight-chain or branched hydrocarbon radicals having 2 to 10 carbon atoms and a double bond in any position (as mentioned above) which are linked to the skeleton via a carbonylamino group (—CONH—);

Alkenylsulfonyl: unsaturated straight-chain or branched hydrocarbon radicals having 2 to 10 carbon atoms and a double bond in any position (as mentioned above) which are linked to the skeleton via a sulfonyl group (—SO$_2$—);

Alkenyloxysulfonyl: a straight-chain or branched alkenyloxy group having 3 to 10 carbon atoms (as mentioned above), which is linked to the skeleton via a sulfonyl group (—SO$_2$—);

Alkenylthiosulfonyl: a straight-chain or branched alkenylthio group having 3 to 10 carbon atoms (as mentioned above), which is linked to the skeleton via a sulfonyl group (—SO$_2$—);

Alkenylaminosulfonyl: a straight-chain or branched alkenylamino group having 3 to 10 carbon atoms (as mentioned above), which is linked to the skeleton via a sulfonyl group (—SO$_2$—);

Alkynyl: straight-chain or branched hydrocarbon groups having 2 to 4, 6, 8 or 10 carbon atoms and a triple bond in any position, eg. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Haloalkynyl: unsaturated straight-chain or branched hydrocarbon radicals having 2 to 10 carbon atoms and a triple bond in any position (as mentioned above), it being possible for some or all of the hydrogen atoms in these groups to be replaced by halogen atoms as mentioned above, in particular fluorine, chlorine and bromine;

Alkynyloxy: unsaturated straight-chain or branched hydrocarbon radicals having 3 to 10 carbon atoms and a triple bond in any position which is not adjacent to the hetero atom (as mentioned above) which are linked to the skeleton via an oxygen atom (—O—);

Haloalkynyloxy: unsaturated straight-chain or branched alkynyloxy groups having 3 to 10 carbon atoms (as mentioned above), it being possible for some or all of the hydrogen atoms in these groups to be replaced by halogen atoms as mentioned above, in particular fluorine, chlorine and bromine;

Alkynylthio: unsaturated straight-chain or branched hydrocarbon radicals having 3 to 10 carbon atoms and a triple bond in any position which is not adjacent to the hetero atom (as mentioned above) which are linked to the skeleton via a sulfur atom (—S—);

Alkynylamino: unsaturated straight-chain or branched hydrocarbon radicals having 3 to 10 carbon atoms and a triple bond in any position which is not adjacent to the hetero atom (as mentioned above) which are linked to the skeleton via an amino group (—NH—);

Alkynylcarbonyl: unsaturated straight-chain or branched hydrocarbon radicals having 2 to 10 carbon atoms and a triple bond in any position (as mentioned above) which are linked to the skeleton via a carbonyl group (—CO—);

Alkynyloxycarbonyl: straight-chain or branched alkynyloxy groups having 3 to 10 carbon atoms (as mentioned above) which are linked to the skeleton via a carbonyl group (—CO—);

Alkynylthiocarbonyl: straight-chain or branched alkynylthio groups having 3 to 10 carbon atoms (as mentioned above) which are linked to the skeleton via a carbonyl group (—CO—);

Alkynylaminocarbonyl: straight-chain or branched alkynylamino groups having 3 to 10 carbon atoms (as mentioned above) which are linked to the skeleton via a carbonyl group (—CO—);

Alkynylcarbonyloxy: unsaturated straight-chain or branched hydrocarbon radicals having 2 to 10 carbon atoms and a triple bond in any position (as mentioned above) which are linked to the skeleton via a carbonyloxy group (—CO$_2$—);

Alkynylcarbonylthio: unsaturated straight-chain or branched hydrocarbon radicals having 2 to 10 carbon atoms and a triple bond in any position (as mentioned above) which are linked to the skeleton via a carbonylthio group (—COS—);

Alkynylcarbonylamino: unsaturated straight-chain or branched hydrocarbon radicals having 2 to 10 carbon atoms and a triple bond in any position (as mentioned above) which are linked to the skeleton via a carbonylamino group (—CONH—);

Alkynylsulfonyl: unsaturated straight-chain or branched hydrocarbon radicals having 2 to 10 carbon atoms and a triple bond in any position (as mentioned above) which are linked to the skeleton via a sulfonyl group (—SO$_2$—);

Alkynyloxysulfonyl: a straight-chain or branched alkynyloxy group having 3 to 10 carbon atoms (as mentioned above), which is linked to the skeleton via a sulfonyl group (—SO$_2$—);

Alkynylthiosulfonyl: a straight-chain or branched alkynylthio group having 3 to 10 carbon atoms (as mentioned above), which is linked to the skeleton via a sulfonyl group (—SO$_2$—);

Alkynylaminosulfonyl: a straight-chain or branched alkynylamino group having 3 to 10 carbon atoms (as mentioned above), which is linked to the skeleton via a sulfonyl group (—SO$_2$—);

Cycloalkyl: monocyclic saturated hydrocarbon groups having 3 to 6, 8, 10 or 12 carbon ring members, eg. $C_3$–$C_8$-cycloalkyl, such as cyclopropyl, cyclobutyl, cyclopentyl, cyclohexyl, cycloheptyl and cyclooctyl;

Cycloalkoxy: monocyclic, saturated hydrocarbon groups having 3 to 12 carbon ring members (as mentioned above) which are linked to the skeleton via an oxygen atom (—O—);

Cycloalkylthio: monocyclic, saturated hydrocarbon groups having 3 to 12 carbon ring members (as mentioned above) which are linked to the skeleton via a sulfur atom (—S—);

Cycloalkylamino: monocyclic, saturated hydrocarbon groups having 3 to 12 carbon ring members (as mentioned above) which are linked to the skeleton via an amino group (—NH—);

Cycloalkylcarbonyl: monocyclic, saturated hydrocarbon groups having 3 to 12 carbon ring members (as mentioned above) which are linked to the skeleton via a carbonyl group (—CO—);

Cycloalkoxycarbonyl: a monocyclic cycloalkoxy group having 3 to 12 carbon ring members (as mentioned above) which is linked to the skeleton via a carbonyl group (—CO—);

Cycloalkylthiocarbonyl: a monocyclic cycloalkylthio group having 3 to 12 carbon ring members (as mentioned above) which is linked to the skeleton via a carbonyl group (—CO—);

Cycloalkylaminocarbonyl: a monocyclic cycloalkylamino group having 3 to 12 carbon ring members (as mentioned above) which is linked to the skeleton via a carbonyl group (—CO—);

Cycloalkylcarbonyloxy: monocyclic saturated hydrocarbon groups having 3 to 12 carbon ring members (as mentioned above) which are linked to the skeleton via a carbonyloxy group (—CO$_2$—);

Cycloalkylcarbonylthio: monocyclic saturated hydrocarbon groups having 3 to 12 carbon ring members (as mentioned above) which are linked to the skeleton via a carbonylthio group (—COS—);

Cycloalkylcarbonylamino: monocyclic saturated hydrocarbon groups having 3 to 12 carbon ring members (as mentioned above) which are linked to the skeleton via a carbonylamino group (—CONH—);

Cycloalkylsulfonyl: monocyclic saturated hydrocarbon groups having 3 to 12 carbon ring members (as mentioned above) which are linked to the skeleton via a sulfonyl group (—SO$_2$—);

Cycloalkoxysulfonyl: a monocyclic cycloalkoxy group having 3 to 12 carbon ring members (as mentioned above) which is linked to the skeleton via a sulfonyl group (—SO$_2$—);

Cycloalkylthiosulfonyl: a monocyclic cycloalkylthio group having 3 to 12 carbon ring members (as mentioned above) which is linked to the skeleton via a sulfonyl group (—SO$_2$—);

Cycloalkylaminosulfonyl: a monocyclic cycloalkylamino group having 3 to 12 carbon ring members (as mentioned above) which is linked to the skeleton via a sulfonyl group (—SO$_2$—);

saturated or partially unsaturated cyclic radical which, besides carbon atoms, may contain hetero atoms from the group consisting of oxygen, sulfur or nitrogen as ring members:

cycloalkyl having 3 to 12 carbon ring members as mentioned above or 5- or 6-membered heterocycles (heterocyclyl) containing, besides carbon ring members, one to three nitrogen atoms and/or one oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl;

Heterocyclyloxy: a 5- or 6-membered heterocycle (as mentioned above) which is linked to the skeleton via an oxygen atom (—O—);

Heterocyclylthio: a 5- or 6-membered heterocycle (as mentioned above) which is linked to the skeleton via a sulfur atom (—S—);

Heterocyclylamino: a 5- or 6-membered heterocycle (as mentioned above) which is linked to the skeleton via an amino group (—NH—);

Heterocyclylcarbonyl: a 5- or 6-membered heterocycle (as mentioned above) which is linked to the skeleton via a carbonyl group (—CO—);

Heterocyclyloxycarbonyl: a heterocyclyloxy group (as mentioned above) which is linked to the skeleton via a carbonyl group (—CO—);

Heterocyclylthiocarbonyl: a heterocyclylthio group (as mentioned above) which is linked to the skeleton via a carbonyl group (—CO—);

Heterocyclylaminocarbonyl: a 5- or 6-membered heterocycle (as mentioned above) which is linked to the skeleton via an aminocarbonyl group (—NHCO—);

Heterocyclylcarbonyloxy: a 5- or 6-membered heterocycle (as mentioned above) which is linked to the skeleton via a carbonyloxy group (—CO$_2$—);

Heterocyclylcarbonylthio: a 5- or 6-membered heterocycle (as mentioned above) which is linked to the skeleton via a carbonylthio group (—COS—);

Heterocyclylcarbonylamino: a 5- or 6-membered heterocycle (as mentioned above) which is linked to the skeleton via a carbonylamino group (—CONH—);

Heterocyclylsulfonyl: a 5- or 6-membered heterocycle (as mentioned above) which is linked to the skeleton via a sulfonyl group (—SO$_2$—);

Aryloxysulfonyl: a heterocyclyloxy group (as mentioned above) which is linked to the skeleton via a sulfonyl group (—SO$_2$—);

Heterocyclylthiosulfonyl: a heterocyclylthio group (as mentioned above) which is linked to the skeleton via a sulfonyl group (—SO$_2$—);

Heterocyclylaminosulfonyl: a heterocyclylamino group (as mentioned above) which is linked to the skeleton via a sulfonyl group (—SO$_2$—);

Aryl: a mono- to trinuclear aromatic ring system containing 6 to 14 carbon ring members, eg. phenyl, naphthyl and anthracenyl;

Aryloxy: a mono- to trinuclear aromatic ring system (as mentioned above) which is linked to the skeleton via an oxygen atom (—O—);

Arylthio: a mono- to trinuclear aromatic ring system (as mentioned above) which is linked to the skeleton via a sulfur atom (—S—);

Arylamino: a mono- to trinuclear aromatic ring system (as mentioned above) which is linked to the skeleton via an amino group (—NH—);

Arylcarbonyl: a mono- to trinuclear aromatic ring system (as mentioned above) which is linked to the skeleton via a carbonyl group (—CO—);

Aryloxycarbonyl: a mono- to trinuclear aryloxy group (as mentioned above) which is linked to the skeleton via a carbonyl group (—CO—);

Arylthiocarbonyl: a mono- to trinuclear arylthio group (as mentioned above) which is linked to the skeleton via a carbonyl group (—CO—);

Arylaminocarbonyl: a mono- to trinuclear arylamino group (as mentioned above) which is linked to the skeleton via a carbonyl group (—CO—);

Arylcarbonyloxy: a mono- to trinuclear aromatic ring system (as mentioned above) which is linked to the skeleton via a carbonyloxy group (—CO$_2$—);

Arylcarbonylthio: a mono- to trinuclear aromatic ring system (as mentioned above) which is linked to the skeleton via a carbonylthio group (—COS—);

Arylcarbonylamino: a mono- to trinuclear aromatic ring system (as mentioned above) which is linked to the skeleton via a carbonylamino group (—CONH—);

Arylsulfonyl: a mono- to trinuclear aromatic ring system (as mentioned above) which is linked to the skeleton via a sulfonyl group (—SO$_2$—);

Aryloxysulfonyl: a mono- to trinuclear aryloxy group (as mentioned above) which is linked to the skeleton via a sulfonyl group (—SO$_2$—);

Arylthiosulfonyl: a mono- to trinuclear arylthio group (as mentioned above) which is linked to the skeleton via a sulfonyl group (—SO$_2$—);

Arylaminosulfonyl: a mono- to trinuclear arylamino group (as mentioned above) which is linked to the skeleton via a sulfonyl group (—SO2—);

aromatic ring system which, besides carbon ring members, may contain hetero atoms from the group consisting of oxygen, sulfur and nitrogen: aryl as mentioned above, or mono- or binuclear heteroaryl, eg.

5-membered heteroaryl containing one to four nitrogen atoms or one to three nitrogen atoms and one sulfur or oxygen atom: 5-membered heteroaryl ring groups, which, besides carbon atoms, may contain one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl containing one to three nitrogen atoms or one nitrogen atom and one oxygen or sulfur atom: 5-membered heteroaryl ring groups which, besides carbon atoms, can contain one to four nitrogen atoms or one to three nitrogen atoms and one sulfur or oxygen atom as ring members and in which two adjacent carbon ring members or one nitrogen and one adjacent carbon ring member can be bridged via a buta-1,3-diene-1,4-diyl group;

5-membered heteroaryl, linked via nitrogen and containing one to four nitrogen atoms, or benzo-fused 5-membered heteroaryl, linked via nitrogen and containing one to three nitrogen atoms: 5-membered heteroaryl ring groups which, besides carbon atoms, can contain one to four nitrogen atoms, or one to three nitrogen atoms, respectively, as ring members and in which two adjacent carbon ring members or one nitrogen and one adjacent carbon ring member can be bridged via a buta-1,3-diene-1,4-diyl group, these rings being linked to the skeleton via one of the nitrogen ring members;

6-membered heteroaryl containing one to three, or one to four, nitrogen atoms, respectively: 6-membered heteroaryl ring groups which, besides carbon atoms, can contain one to three, or one to four, nitrogen atoms, respectively, as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Hetaryloxy: a mono- to trinuclear heteroaromatic ring system (as mentioned above) which is linked to the skeleton via an oxygen atom (—O—);

Hetarylthio: a mono- to trinuclear heteroaromatic ring system (as mentioned above) which is linked to the skeleton via a sulfur atom (—S—);

Hetarylamino: a mono- to trinuclear heteroaromatic ring system (as mentioned above) which is linked to the skeleton via an amino group (—NH—);

Hetarylcarbonyl: a mono- to trinuclear heteroaromatic ring system (as mentioned above) which is linked to the skeleton via a carbonyl group (—CO—);

Hetaryloxycarbonyl: a mono- to trinuclear hetaryloxy group (as mentioned above) which is linked to the skeleton via a carbonyl group (—CO—);

Hetarylthiocarbonyl: a mono- to trinuclear hetarylthio group (as mentioned above) which is linked to the skeleton via a carbonyl group (—CO—);

Hetarylaminocarbonyl: a mono- to trinuclear hetarylamino group (as mentioned above) which is linked to the skeleton via a carbonyl group (—CO—);

Hetarylcarbonyloxy: a mono- to trinuclear heteroaromatic ring system (as mentioned above) which is linked to the skeleton via a carbonyloxy group (—CO$_2$—);

Hetarylcarbonylthio: a mono- to trinuclear heteroaromatic ring system (as mentioned above) which is linked to the skeleton via a carbonylthio group (—COS—);

Hetarylcarbonylamino: a mono- to trinuclear heteroaromatic ring system (as mentioned above) which is linked to the skeleton via a carbonylamino group (—CONH—);

Hetarylsulfonyl: a mono- to trinuclear heteroaromatic ring system (as mentioned above) which is linked to the skeleton via a sulfonyl group (—SO$_2$—);

Hetaryloxysulfonyl: a mono- to trinuclear hetaryloxy group (as mentioned above) which is linked to the skeleton via a sulfonyl group (—SO$_2$—);

Hetarylthiosulfonyl: a mono- to trinuclear hetarylthio group (as mentioned above) which is linked to the skeleton via a sulfonyl group (—SO$_2$—);

Hetarylaminosulfonyl: a mono- to trinuclear hetarylamino group (as mentioned above) which is linked to the skeleton via a sulfonyl group (—SO$_2$—);

Alkylene: divalent unbranched chains of 3 to 5 CH$_2$-groups, eg. CH$_2$, CH$_2$CH$_2$, CH$_2$CH$_2$CH$_2$, CH$_2$CH$_2$CH$_2$CH$_2$ and CH$_2$CH$_2$CH$_2$CH$_2$CH$_2$;

Oxyalkylene: divalent unbranched chains of 2 to 4 CH$_2$-groups, one valency being linked to the skeleton via an oxygen atom, eg. OCH$_2$CH$_2$, OCH$_2$CH$_2$CH$_2$ and OCH$_2$CH$_2$CH$_2$CH$_2$;

Oxyalkyleneoxy: divalent unbranched chains of 1 to 3 CH$_2$-groups, both valancies being linked to the skeleton via an oxygen atom, eg. OCH$_2$O, OCH$_2$CH$_2$O and OCH$_2$CH$_2$CH$_2$O;

Alkenylene: divalent unbranched chains of 1 to 3 CH$_2$-groups and one CH=CH-group in any position, eg. CH=CHCH$_2$, CH$_2$CH=CHCH$_2$, CH=CHCH$_2$CH$_2$, CH$_2$CH=CHCH$_2$CH$_2$ and CH=CHCH$_2$CH$_2$CH$_2$;

Oxyalkenylene: divalent unbranched chains of 0 to 2 CH$_2$-groups and one CH=CH-group in any position, one valancy being linked to the skeleton via an oxygen atom, eg. OCH=CH, OCH=CHCH$_2$, OCH$_2$CH=CH, OCH$_2$CH=CHCH$_2$, OCH=CHCH$_2$CH$_2$ and OCH$_2$CH$_2$—CH=CH;

Oxyalkenyleneoxy: divalent unbranched chains of 0 to 2 CH$_2$-groups and one CH=CH-group in any position, both valencies being linked to the skeleton via an oxygen atom, eg. OCH=CHO, OCH=CHCH$_2$O, OCH$_2$CH=CHCH$_2$O and OCH=CHCH$_2$CH$_2$O;

organic radical: unsubstituted or substituted alkyl, alkenyl, alkynyl, cycloalkyl, heterocyclyl, aryl or hetaryl.

The term "unsubstituted or substituted" when relating to alkyl, alkenyl and alkynyl groups is intended to express that these groups can be partially or fully halogenated [i.e. some or all of the hydrogen atoms of these groups can be replaced by identical or different halogen atoms as mentioned above (preferably fluorine, chlorine or bromine)] and/or can have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular containing 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals containing preferably 1 to 6 carbon atoms, in particular 1 to 4 carbon atoms.

The term "unsubstituted or substituted" when relating to the cyclic (saturated, unsaturated or aromatic) groups is intended to express that these groups can be partially or fully halogenated [i.e. some or all of the hydrogen atoms in these groups can be replaced by identical or different halogen atoms as mentioned above (preferably fluorine, chlorine or bromine, in particular fluorine or chlorine)] and/or can have attached to them one to four (in particular one to three) of the following radicals:

cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkoxycarbonyl-N-alkylamino, the alkyl groups in these radicals preferably containing 1 to 6 carbon atoms, in particular 1 to 4 carbon atoms, and the abovementioned alkenyl or alkynyl groups in these radicals containing 2 to 8, preferably 2 to 6, in particular 2 to 4, carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon toms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to ring members, in particular 6 ring members (phenyl), the hetaryl radicals containing in particular 5 or 6 ring members and the alkyl groups in the radicals preferably containing 1 to 6 carbon atoms, in particular 1 to 4 carbon atoms;

and/or one or two (in particular one) of the following radicals:

formyl, $CR^{iii}$=$NOR^{iv}$ [where $R^{iii}$ is hydrogen, alkyl, cycloalkyl and aryl and $R^{iv}$ is alkyl, alkenyl, haloalkenyl, alkynyl and arylalkyl (the abovementioned alkyl groups preferably containing 1 to 6 carbon atoms, in particular 1 to 4 carbon atoms, the abovementioned cycloalkyl groups, alkenyl groups and alkynyl groups preferably containing from 3 to 8, in particular 3 to 6, carbon atoms) and aryl being in particular phenyl which is unsubstituted or can be substituted by customary groups] or $NR^{v}$—CO—D—$R^{vi}$ [where $R^{v}$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl, $R^{vi}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl and D being a direct linkage, oxygen or nitrogen, it being possible for the nitrogen to have attached to it one of the groups mentioned under $R^{vi}$], and/or where two adjacent C-atoms of the cyclic systems can have attached to them a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group, it being possible for these bridges, in turn, to be partially or fully halogenated and/or to have attached to them one to three, in particular one or two, of the following radicals:

$C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are to be understood as meaning, in particular, the following substituents: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

Especially preferred compounds I are those where Q is $C(CO_2CH_3)$=$CHCH_3$, $C(CO_2CH_3)$=$CHOCH_3$, $C(CONH_2)$=$NOCH_3$, $C(CONHCH_3)$=$NOCH_3$ or $N(OCH_3)$—$CO_2CH_3$.

Especially preferred compounds of the formula I are those where $R^1$ is hydrogen or one of the following groups: unsubstituted or substituted alkyl, alkenyl, alkynyl, cycloalkyl, heterocyclyl, aryl or heteroaryl.

Particularly preferred compounds I are those where $R^1$ is hydrogen.

Furthermore, especially preferred compounds I are those where $R^1$ is unsubstituted or substituted $C_1$–$C_6$-alkyl.

Equally, especially preferred compounds I are those where $R^1$ is unsubstituted or substituted $C_3$–$C_6$-alkenyl.

Besides, especially preferred compounds I are those where $R^1$ is unsubstituted or substituted $C_3$–$C_6$-alkynyl.

Other particularly preferred compounds I are those where $R^1$ is $C_1$–$C_6$-haloalkyl.

Furthermore, especially preferred compounds I are those where $R^1$ is $C_3$–$C_6$-haloalkenyl.

Equally, especially preferred compounds I are those where $R^1$ is aryl-$C_1$–$C_2$-alkyl, it being possible for the aryl radical to be unsubstituted or substituted.

Especially preferred compounds I are those where $R^1$ is aryl-$C_1$–$C_2$-alkyl, it being possible for the aryl radical to be partially or fully halogenated and/or to have attached to it one to three of the following groups: $C_1$–$C_4$-alkyl, $C_1$–$C_4$-haloalkyl and $C_1$–$C_4$-alkoxy.

Besides, especially preferred compounds I are those where $R^1$ is $C_3$–$C_6$-cycloalkyl-$C_1$–$C_2$-alkyl, it being possible for the cycloalkyl radical to be unsubstituted or substituted.

Particularly preferred compounds I are those where $R^1$ is $C_3$–$C_6$-cycloalkyl-$C_1$–$C_2$-alkyl, it being possible for the cycloalkyl radical to be partially or fully halogenated and/or to have attached to it one to three $C_1$–$C_4$-alkyl groups.

Moreover, especially preferred compounds I are those where $R^1$ is hetaryl-$C_1$–$C_2$-alkyl, it being possible for the hetaryl radical to be unsubstituted or substituted.

Particularly preferred compounds I are those where $R^1$ is hetaryl-$C_1$–$C_2$-alkyl, it being possible for the hetaryl radical to be partially or fully halogenated and/or to have attached to it one to three of the following groups: $C_1$–$C_4$-alkyl, $C_1$–$C_4$-haloalkyl and $C_1$–$C_4$-alkoxy.

Furthermore, especially preferred compounds of the formula I are those where $R^2$ is hydrogen or one of the following groups: unsubstituted or substituted alkyl, alkenyl, alkynyl, cycloalkyl, heterocyclyl, aryl or hetaryl, these groups being linked to the skeleton either directly (via a carbon atom) or via an oxygen, sulfur or nitrogen atom.

Particularly preferred compounds I are those where $R^2$ is unsubstituted or substituted $C_1$–$C_6$-alkyl.

Furthermore, especially preferred compounds I are those where $R^2$ is unsubstituted or substituted $C_2$–$C_6$-alkenyl.

Equally, especially preferred compounds I are those where $R^2$ is unsubstituted or substituted $C_2$–$C_6$-alkynyl.

Besides, especially preferred compounds I are those where $R^2$ is $C_3$–$C_6$-cycloalkyl.

Other compounds I which are particularly preferred are those where $R^2$ is aryl.

Furthermore, especially preferred compounds I are those where $R^2$ is hetaryl.

Moreover, especially preferred compounds I are those where x is 0, 1 or 2, it being possible for the radicals $R^3$ to be different if x is 2.

Particularly preferred compounds I are those where x is 0 or 1.

Furthermore, especially preferred compounds of the formula I are those where $R^3$ is cyano, nitro, halogen or one of the following groups: unsubstituted or substituted alkyl, alkenyl, alkynyl, cycloalkyl, heterocyclyl, aryl or hetaryl, these groups being linked to the skeleton directly (via a carbon atom) or via an oxygen, sulfur or nitrogen atom.

Particularly preferred compounds I are those where $R^3$ is halogen, in particular fluorine, chlorine and bromine.

Furthermore, especially preferred compounds I are those where $R^3$ is $C_1$–$C_2$-alkyl.

Equally, especially preferred compounds I are those where $R^3$ is $C_1$–$C_2$-alkoxy.

Besides, especially preferred compounds I are those where $R^3$ is cyano.

Other particularly preferred compounds I are those where $R^3$ is nitro.

Moreover, especially preferred compounds I are those where y is 0, 1, 2 or 3, it being possible for the radicals $R^4$ to be different if y is 2 or 3.

Particularly preferred compounds I are those where y is 0 or 1.

Furthermore, especially preferred compounds I are those where $R^4$ is cyano, halogen, $C_1$–$C_3$-alkyl, $C_1$–$C_2$-haloalkyl or $C_1$–$C_3$-alkoxy, in particular cyano, fluorine, chlorine, methyl, ethyl, isopropyl, trifluoromethyl, methoxy or ethoxy.

Particularly preferred compounds I are those where $R^4$ is methyl.

Furthermore, especially preferred compounds I are those where $R^4$ is methoxy.

Equally, especially preferred compounds I are those where $R^4$ is fluorine.

Besides, especially preferred compounds I are those where $R^4$ is chlorine.

Other particularly preferred compounds I are those where $R^4$ is trifluoromethyl.

Furthermore, especially preferred compounds I are those where $R^4$ is $OCH_2O$.

Particularly preferred compounds I with a view to their use are those compiled in the tables which follow. Furthermore, the groups mentioned in the tables for one substituent are as such an especially preferred embodiment of the substituent in question, irrespective of the combination in which they are mentioned.

Table 1

Compounds of the general formula IA.1 where $R^2$ is methyl and $R^1$ for a compound corresponds in each case to a group of Table A

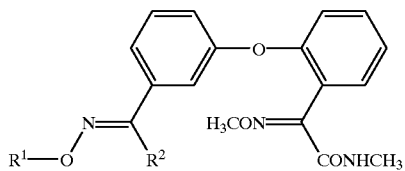

IA.1

Table 2

Compounds of the general formula IA.2 where $R^2$ is methyl and $R^1$ for a compound corresponds in each case to a group of Table A

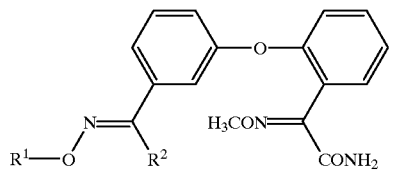

IA.2

Table 3

Compounds of the general formula IA.3, where $R^2$ is methyl and $R^1$ for a compound corresponds in each case to a group of Table A

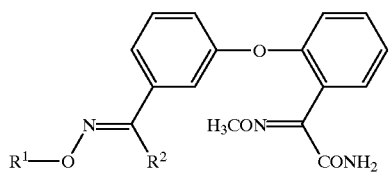

IA.2

Table 4

Compounds of the general formula IA.4, where $R^2$ is methyl and $R^1$ for a compound corresponds in each case to a group of Table A

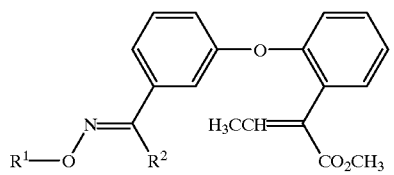

IA.4

Table 5

Compounds of the general formula IA.5, where $R^2$ is methyl and $R^1$ for a compound corresponds in each case to a group of Table A

IA.4

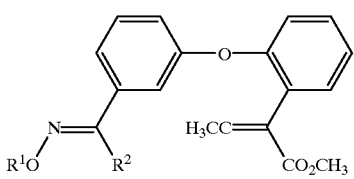

Table 6

Compounds of the general formula IA.1, where $R^1$ is methyl and $R^2$ for a compound corresponds in each case to a group of Table B Table 7

Compounds of the general formula IA.2, where $R^1$ is methyl and $R^2$ for a compound corresponds in each case to a group of Table B Table 8

Compounds of the general formula IA.3, where $R^1$ is methyl and $R^2$ for a compound corresponds in each case to a group of Table B Table 9

Compounds of the general formula IA.4, where $R^1$ is methyl and $R^2$ for a compound corresponds in each case to a group of Table B Table 10

Compounds of the general formula IA.5, where $R^1$ is methyl and $R^2$ for a compound corresponds in each case to a group of Table B

TABLE A

| No. | $R^1$ |
|---|---|
| A.1 | H |
| A.2 | $CH_3$ |
| A.3 | $C_2H_5$ |
| A.4 | $n-C_3H_7$ |
| A.5 | $i-C_3H_7$ |
| A.6 | cyclopropyl |
| A.7 | $n-C_4H_9$ |
| A.8 | $s-C_4H_9$ |
| A.9 | $i-C_4H_9$ |
| A.10 | $t-C_4H_9$ |
| A.11 | $n-C_5H_{11}$ |
| A.12 | $i-C_5H_{11}$ |
| A.13 | $neo-C_5H_{11}$ |
| A.14 | cyclopentyl |
| A.15 | $n-C_6H_{13}$ |
| A.16 | cyclohexyl |
| A.17 | $n-C_8H_{17}$ |
| A.18 | $CH_2CH_2Cl$ |
| A.19 | $(CH_2)_4Cl$ |
| A.20 | $CH_2CN$ |
| A.21 | $CH_2CH_2CN$ |
| A.22 | $(CH_2)_3CN$ |
| A.23 | $(CH_2)_4CN$ |
| A.24 | $(CH_2)_6CN$ |
| A.25 | cyclohexylmethyl |
| A.26 | 2-cyclohexyleth-1-yl |
| A.27 | cyclopropylmethyl |
| A.28 | 2-cyclopropyleth-1-yl |

TABLE A-continued

| No. | $R^1$ |
|---|---|
| A.29 | 2-methoxyeth-1-yl |
| A.30 | 2-ethoxyeth-1-yl |
| A.31 | 2-isopropoxyeth-1-yl |
| A.32 | 3-methoxyprop-1-yl |
| A.33 | 3-ethoxyprop-1-yl |
| A.34 | 3-isopropoxyprop-1-yl |
| A.35 | 4-methoxybut-1-yl |
| A.36 | 4-isopropoxybut-1-yl |
| A.37 | propen-3-yl |
| A.38 | but-2-en-1-yl |
| A.39 | 3-methylbut-2-en-1-yl |
| A.40 | 2-vinyloxyeth-1-yl |
| A.41 | allyloxyeth-1-yl |
| A.42 | 2-trifluoromethoxyeth-1-yl |
| A.43 | 3-trifluoromethoxyprop-1-yl |
| A.44 | 4-difluoromethoxybut-1-yl |
| A.45 | hydroxycarbonylmethyl |
| A.46 | methoxycarbonylmethyl |
| A.47 | aminocarbonylmethyl |
| A.48 | N-methylaminocarbonylmethyl |
| A.49 | N,N-dimethylaminocarbonyl-methyl |
| A.50 | 2-hydroxycarbonyleth-1-yl |
| A.51 | 2-methoxycarbonyleth-1-yl |
| A.52 | 2-aminocarbonyleth-1-yl |
| A.53 | 2-N-methylaminocarbonyleth-1-yl |
| A.54 | 2-dimethylaminocarbonyleth-1-yl |
| A.55 | 2-aminoeth-1-yl |
| A.56 | 2-aminoprop-1-yl |
| A.57 | 4-aminobut-1-yl |
| A.58 | 3-dimethylaminoprop-1-yl |
| A.59 | 4-aminothiocarbonylbut-1-yl |
| A.60 | 2-oxopropyl |
| A.61 | cyclohexyl |
| A.62 | cyclopropyl |
| A.63 | cyclopentyl |
| A.64 | 2-methoxyiminoprop-1-yl |
| A.65 | 2-methoxyiminoeth-1-yl |
| A.66 | 6-aminocarbonylhex-1-yl |
| A.67 | 3-aminothiocarbonylprop-1-yl |
| A.68 | 2-aminothiocarbonyleth-1-yl |
| A.69 | aminothiocarbonylmethyl |
| A.70 | 4-(N,N-dimethylamino)but-1-yl |
| A.71 | 2-(methylthio)eth-1-yl |
| A.72 | 2-(methylsulfonyl)eth-1-yl |
| A.73 | 4-(methylthio)prop-1-yl |
| A.74 | 4-(methylsulfonyl)prop-1-yl |
| A.75 | benzyl |
| A.76 | $2-F-C_6H_4-CH_2$ |
| A.77 | $3-F-C_6H_4-CH_2$ |
| A.78 | $4-F-C_6H_4-CH_2$ |
| A.79 | $2,3-F_2-C_6H_3-CH_2$ |
| A.80 | $2,4-F_2-C_6H_3-CH_2$ |
| A.81 | $2,5-F_2-C_6H_3-CH_2$ |
| A.82 | $2,6-F_2-C_6H_3-CH_2$ |
| A.83 | $3,4-F_2-C_6H_3-CH_2$ |
| A.84 | $3,5-F_2-C_6H_3-CH_2$ |
| A.85 | $2-Cl-C_6H_4-CH_2$ |
| A.86 | $3-Cl-C_6H_4-CH_2$ |
| A.87 | $4-Cl-C_6H_4-CH_2$ |
| A.88 | $2,3-Cl_2-C_6H_3-CH_2$ |
| A.89 | $2,4-Cl_2-C_6H_3-CH_2$ |
| A.90 | $2,5-Cl_2-C_6H_3-CH_2$ |
| A.91 | $2,6-Cl_2-C_6H_3-CH_2$ |
| A.92 | $3,4-Cl_2-C_6H_3-CH_2$ |
| A.93 | $3,5-Cl_2-C_6H_3-CH_2$ |
| A.94 | $2,3,4-Cl_3-C_6H_2-CH_2$ |
| A.95 | $2,3,5-Cl_3-C_6H_2-CH_2$ |
| A.96 | $2,3,6-Cl_3-C_6H_2-CH_2$ |
| A.97 | $2,4,5-Cl_3-C_6H_2-CH_2$ |
| A.98 | $2,4,6-Cl_3-C_6H_2-CH_2$ |
| A.99 | $3,4,5-Cl_3-C_6H_2-CH_2$ |
| A.100 | $2-Br-C_6H_4-CH_2$ |
| A.101 | $3-Br-C_6H_4-CH_2$ |
| A.102 | $4-Br-C_6H_4-CH_2$ |
| A.103 | $2,3-Br_2-C_6H_3-CH_2$ |
| A.104 | $2,4-Br_2-C_6H_3-CH_2$ |
| A.105 | $2,5-Br_2-C_6H_3-CH_2$ |

TABLE A-continued

| No. | R¹ |
| --- | --- |
| A.106 | 2,6-Br$_2$—C$_6$H$_3$—CH$_2$ |
| A.107 | 3,4-Br$_2$—C$_6$H$_3$—CH$_2$ |
| A.108 | 3,5-Br$_2$—C$_6$H$_3$—CH$_2$ |
| A.109 | 2-F, 3-Cl—C$_6$H$_3$—CH$_2$ |
| A.110 | 2-F, 4-Cl—C$_6$H$_3$—CH$_2$ |
| A.111 | 2-F, 5-Cl—C$_6$H$_3$—CH$_2$ |
| A.112 | 2-F, 3-Br—C$_6$H$_3$—CH$_2$ |
| A.113 | 2-F, 4-Br—C$_6$H$_3$—CH$_2$ |
| A.114 | 2-F, 5-Br—C$_6$H$_3$—CH$_2$ |
| A.115 | 2-Cl, 3-Br—C$_6$H$_3$—CH$_2$ |
| A.116 | 2-Cl, 4-Br—C$_6$H$_3$—CH$_2$ |
| A.117 | 2-Cl, 5-Br—C$_6$H$_3$—CH$_2$ |
| A.118 | 3-F, 4-Cl—C$_6$H$_3$—CH$_2$ |
| A.119 | 3-F, 5-Cl—C$_6$H$_3$—CH$_2$ |
| A.120 | 3-F, 6-Cl—C$_6$H$_3$—CH$_2$ |
| A.121 | 3-F, 4-Br—C$_6$H$_3$—CH$_2$ |
| A.122 | 3-F, 5-Br—C$_6$H$_3$—CH$_2$ |
| A.123 | 3-F, 6-Br—C$_6$H$_3$—CH$_2$ |
| A.124 | 3-Cl, 4-Br—C$_6$H$_3$—CH$_2$ |
| A.125 | 3-Cl, 5-Br—C$_6$H$_3$—CH$_2$ |
| A.126 | 3-Cl, 6-Br—C$_6$H$_3$—CH$_2$ |
| A.127 | 4-F, 5-Cl—C$_6$H$_3$—CH$_2$ |
| A.128 | 4-F, 6-Cl—C$_6$H$_3$—CH$_2$ |
| A.129 | 4-F, 5-Br—C$_6$H$_3$—CH$_2$ |
| A.130 | 4-F, 6-Br—C$_6$H$_3$—CH$_2$ |
| A.131 | 4-Cl, 5-Br—C$_6$H$_3$—CH$_2$ |
| A.132 | 5-F, 6-Cl—C$_6$H$_3$—CH$_2$ |
| A.133 | 5-F, 6-Br—C$_6$H$_3$—CH$_2$ |
| A.134 | 5-Cl, 6-Br—C$_6$H$_3$—CH$_2$ |
| A.135 | 3-Br, 4-Cl, 5-Br—C$_6$H$_2$—CH$_2$ |
| A.136 | 2-CN—C$_6$H$_4$—CH$_2$ |
| A.137 | 3-CN—C$_6$H$_4$—CH$_2$ |
| A.138 | 4-CN—C$_6$H$_4$—CH$_2$ |
| A.139 | 2-NO$_2$—C$_6$H$_4$—CH$_2$ |
| A.140 | 3-NO$_2$—C$_6$H$_4$—CH$_2$ |
| A.141 | 4-NO$_2$—C$_6$H$_4$—CH$_2$ |
| A.142 | 2-CH$_3$—C$_6$H$_4$—CH$_2$ |
| A.143 | 3-CH$_3$—C$_6$H$_4$—CH$_2$ |
| A.144 | 4-CH$_3$—C$_6$H$_4$—CH$_2$ |
| A.145 | 2,3-(CH$_3$)$_2$—C$_6$H$_3$—CH$_2$ |
| A.146 | 2,4-(CH$_3$)$_2$—C$_6$H$_3$—CH$_2$ |
| A.147 | 2,5-(CH$_3$)$_2$—C$_6$H$_3$—CH$_2$ |
| A.148 | 2,6-(CH$_3$)$_2$—C$_6$H$_3$—CH$_2$ |
| A.149 | 3,4-(CH$_3$)$_2$—C$_6$H$_3$—CH$_2$ |
| A.150 | 3,5-(CH$_3$)$_2$—C$_6$H$_3$—CH$_2$ |
| A.151 | 2-C$_2$H$_5$—C$_6$H$_4$—CH$_2$ |
| A.152 | 3-C$_2$H$_5$—C$_6$H$_4$—CH$_2$ |
| A.153 | 4-C$_2$H$_5$—C$_6$H$_4$—CH$_2$ |
| A.154 | 2-i-C$_3$H$_7$—C$_6$H$_4$—CH$_2$ |
| A.155 | 3-i-C$_3$H$_7$—C$_6$H$_4$—CH$_2$ |
| A.156 | 4-i-C$_3$H$_7$—C$_6$H$_4$—CH$_2$ |
| A.157 | 2-cyclohexyl-C$_6$H$_4$—CH$_2$ |
| A.158 | 3-cyclohexyl-C$_6$H$_4$—CH$_2$ |
| A.159 | 4-cyclohexyl-C$_6$H$_4$—CH$_2$ |
| A.160 | 2-vinyl-C$_6$H$_4$—CH$_2$ |
| A.161 | 3-vinyl-C$_6$H$_4$—CH$_2$ |
| A.162 | 4-vinyl-C$_6$H$_4$—CH$_2$ |
| A.163 | 2-allyl-C$_6$H$_4$—CH$_2$ |
| A.164 | 3-allyl-C$_6$H$_4$—CH$_2$ |
| A.165 | 4-allyl-C$_6$H$_4$—CH$_2$ |
| A.166 | 2-C$_6$H$_5$—C$_6$H$_4$—CH$_2$ |
| A.167 | 3-C$_6$H$_5$—C$_6$H$_4$—CH$_2$ |
| A.168 | 4-C$_6$H$_5$—C$_6$H$_4$—CH$_2$ |
| A.169 | 3-CH$_3$, 5-t-C$_4$H$_9$—C$_6$H$_3$—CH$_2$ |
| A.170 | 2-OH-C$_6$H$_4$—CH$_2$ |
| A.171 | 3-OH-C$_6$H$_4$—CH$_2$ |
| A.172 | 4-OH-C$_6$H$_4$—CH$_2$ |
| A.173 | 2-OCH$_3$—C$_6$H$_4$—CH$_2$ |
| A.174 | 3-OCH$_3$—C$_6$H$_4$—CH$_2$ |
| A.175 | 4-OCH$_3$—C$_6$H$_4$—CH$_2$ |
| A.176 | 2,3-(OCH$_3$)$_2$—C$_6$H$_3$—CH$_2$ |
| A.177 | 2,4-(OCH$_3$)$_2$—C$_6$H$_3$—CH$_2$ |
| A.178 | 2,5-(OCH$_3$)$_2$—C$_6$H$_3$—CH$_2$ |
| A.179 | 3,4-(OCH$_3$)$_2$—C$_6$H$_3$—CH$_2$ |
| A.180 | 3,5-(OCH$_3$)$_2$—C$_6$H$_3$—CH$_2$ |
| A.181 | 3,4,5-(OCH$_3$)$_3$—C$_6$H$_2$—CH$_2$ |
| A.182 | 2-OC$_2$H$_5$—C$_6$H$_4$—CH$_2$ |
| A.183 | 3-OC$_2$H$_5$—C$_6$H$_4$—CH$_2$ |
| A.184 | 4-OC$_2$H$_5$—C$_6$H$_4$—CH$_2$ |
| A.185 | 2-O-(n-C$_3$H$_7$)—C$_6$H$_4$—CH$_2$ |
| A.186 | 3-O-(n-C$_3$H$_7$)—C$_6$H$_4$—CH$_2$ |
| A.187 | 4-O-(n-C$_3$H$_7$)—C$_6$H$_4$—CH$_2$ |
| A.188 | 2-O-(i-C$_3$H$_7$)—C$_6$H$_4$—CH$_2$ |
| A.189 | 3-O-(i-C$_3$H$_7$)—C$_6$H$_4$—CH$_2$ |
| A.190 | 4-O-(i-C$_3$H$_7$)—C$_6$H$_4$—CH$_2$ |
| A.191 | 4-O-(n-C$_4$H$_9$)—C$_6$H$_4$—CH$_2$ |
| A.192 | 3-O-(t-C$_4$H$_9$)—C$_6$H$_4$—CH$_2$ |
| A.193 | 4-O-(n-C$_6$H$_{13}$)—C$_6$H$_4$—CH$_2$ |
| A.194 | 2-O-Allyl-C$_6$H$_4$—CH$_2$ |
| A.195 | 3-O-Allyl-C$_6$H$_4$—CH$_2$ |
| A.196 | 4-O-Allyl-C$_6$H$_4$—CH$_2$ |
| A.197 | 2-CF$_3$—C$_6$H$_4$—CH$_2$ |
| A.198 | 3-CF$_3$—C$_6$H$_4$—CH$_2$ |
| A.199 | 4-CF$_3$—C$_6$H$_4$—CH$_2$ |
| A.200 | 2-acetyl-C$_6$H$_4$—CH$_2$ |
| A.201 | 3-acetyl-C$_6$H$_4$—CH$_2$ |
| A.202 | 4-acetyl-C$_6$H$_4$—CH$_2$ |
| A.203 | 2-methoxycarbonyl-C$_6$H$_4$—CH$_2$ |
| A.204 | 3-methoxycarbonyl-C$_6$H$_4$—CH$_2$ |
| A.205 | 4-methoxycarbonyl-C$_6$H$_4$—CH$_2$ |
| A.206 | 2-aminocarbonyl-C$_6$H$_4$—CH$_2$ |
| A.207 | 3-aminocarbonyl-C$_6$H$_4$—CH$_2$ |
| A.208 | 4-aminocarbonyl-C$_6$H$_4$—CH$_2$ |
| A.209 | 2-dimethylaminocarbonyl-C$_6$H$_4$—CH$_2$ |
| A.210 | 3-dimethylaminocarbonyl-C$_6$H$_4$—CH$_2$ |
| A.211 | 4-dimethylaminocarbonyl-C$_6$H$_4$—CH$_2$ |
| A.212 | 2-(N-methylaminocarbonyl)-C$_6$H$_4$—CH$_2$ |
| A.213 | 3-(N-methylaminocarbonyl)-C$_6$H$_4$—CH$_2$ |
| A.214 | 4-(N-methylaminocarbonyl)-C$_6$H$_4$—CH$_2$ |
| A.215 | 2-H$_2$N—C$_6$H$_4$—CH$_2$ |
| A.216 | 3-H$_2$N—C$_6$H$_4$—CH$_2$ |
| A.217 | 4-H$_2$N—C$_6$H$_4$—CH$_2$ |
| A.218 | 2-aminothiocarbonyl-C$_6$H$_4$—CH$_2$ |
| A.219 | 3-aminothiocarbonyl-C$_6$H$_4$—CH$_2$ |
| A.220 | 4-aminothiocarbonyl-C$_6$H$_4$—CH$_2$ |
| A.221 | 2-methoxyiminomethyl-C$_6$H$_4$—CH$_2$ |
| A.222 | 3-methoxyiminomethyl-C$_6$H$_4$—CH$_2$ |
| A.223 | 4-methoxyiminomethyl-C$_6$H$_4$—CH$_2$ |
| A.224 | 2-formyl-C$_6$H$_4$—CH$_2$ |
| A.225 | 3-formyl-C$_6$H$_4$—CH$_2$ |
| A.226 | 4-formyl-C$_6$H$_4$—CH$_2$ |
| A.227 | 2-(1'methoxyiminoeth-1'-yl)-C$_6$H$_4$—CH$_2$ |
| A.228 | 3-(1'-methoxyiminoeth-1'-yl)-C$_6$H$_4$—CH$_2$ |
| A.229 | 4-(1'-methoxyiminoeth-1'-yl)-C$_6$H$_4$—CH$_2$ |
| A.230 | 2-SCH$_3$—C$_6$H$_4$—CH$_2$ |
| A.231 | 3-SCH$_3$—C$_6$H$_4$—CH$_2$ |
| A.232 | 4-SCH$_3$—C$_6$H$_4$—CH$_2$ |
| A.233 | 2-SO$_2$CH$_3$—C$_6$H$_4$—CH$_2$ |
| A.234 | 3-SO$_2$CH$_3$—C$_6$H$_4$—CH$_2$ |
| A.235 | 4-SO$_2$CH$_3$—C$_6$H$_4$—CH$_2$ |
| A.236 | 2-OCF$_3$—C$_6$H$_4$—CH$_2$ |
| A.237 | 3-OCF$_3$—C$_6$H$_4$—CH$_2$ |
| A.238 | 4-OCF$_3$—C$_6$H$_4$—CH$_2$ |
| A.239 | 2-OCHF$_2$—C$_6$H$_4$—CH$_2$ |
| A.240 | 3-OCHF$_2$—C$_6$H$_4$—CH$_2$ |
| A.241 | 4-OCHF$_2$—C$_6$H$_4$—CH$_2$ |
| A.242 | 3-CF$_3$, 4-OCF$_3$—C$_6$H$_3$—CH$_2$ |
| A.243 | 1-naphthyl-CH$_2$ |
| A.244 | 2-naphthyl-CH$_2$ |
| A.245 | 2-phenoxyeth-1-yl |
| A.246 | 2-(2'-chlorophenoxy)eth-1-yl |
| A.247 | 2-(3'-chlorophenoxy)eth-1-yl |
| A.248 | 2-(4'-chlorophenoxy)eth-1-yl |
| A.249 | 2-(3',5'-dichlorophenoxy)eth-1-yl |
| A.250 | 2-(2'-cyanophenoxy)eth-1-yl |
| A.251 | 2-(3'-cyanophenoxy)eth-1-yl |
| A.252 | 2-(4'-cyanophenoxy)eth-1-yl |
| A.253 | 2-(2'-methylphenoxy)eth-1-yl |
| A.254 | 2-(3'-methylphenoxy)eth-1-yl |
| A.255 | 2-(4'-methylphenoxy)eth-1-yl |
| A.256 | 2-(3'-t-butylphenoxy)eth-1-yl |
| A.257 | 2-(4'-t-butylphenoxy)eth-1-yl |
| A.258 | 2-(2'-nitrophenoxy)eth-1-yl |
| A.259 | 2-(3'-nitrophenoxy)eth-1-yl |

TABLE A-continued

| No. | R¹ |
|---|---|
| A.260 | 2-(4'-nitrophenoxy)eth-1-yl |
| A.261 | 2-(2'-methoxyphenoxy)eth-1-yl |
| A.262 | 2-(3'-methoxyphenoxy)eth-1-yl |
| A.263 | 2-(4'-methoxyphenoxy)eth-1-yl |
| A.264 | 2-(2'-trifluoromethylphenoxy)eth-1-yl |
| A.265 | 2-(3'-trifluoromethylphenoxy)eth-1-yl |
| A.266 | 2-(4'-trifluoromethylphenoxy)eth-1-yl |
| A.267 | 2-(2'-acetylphenoxy)eth-1-yl |
| A.268 | 2-(3'-acetylphenoxy)eth-1-yl |
| A.269 | 2-(4'-acetylphenoxy)eth-1-yl |
| A.270 | 2-(2'-methoxycarbonyl)eth-1-yl |
| A.271 | 2-(3'-methoxycarbonyl)eth-1-yl |
| A.272 | 2-(4'-methoxycarbonyl)eth-1-yl |
| A.273 | 2-(2'-dimethylaminocarbonyl)eth-1-yl |
| A.274 | 2-(3'-dimethylaminocarbonyl)eth-1-yl |
| A.275 | 2-(4'-dimethylaminocarbonyl)eth-1-yl |
| A.276 | 2-(2'-aminothiocarbonyl)eth-1-yl |
| A.277 | 2-(3'-aminothiocarbonyl)eth-1-yl |
| A.278 | 2-(4'-aminothiocarbonyl)eth-1-yl |
| A.279 | 2-(2'-methylsulfonyl)eth-1-yl |
| A.280 | 2-(3'-methylsulfonyl)eth-1-yl |
| A.281 | 2-(4'-methylsulfonyl)eth-1-yl |
| A.282 | 3-phenoxyprop-1-yl |
| A.283 | 3-(2'-chlorophenoxy)prop-1-yl |
| A.284 | 3-(3'-chlorophenoxy)prop-1-yl |
| A.285 | 3-(4'-chlorophenoxy)prop-1-yl |
| A.286 | 3-(3',5',dichlorophenoxy)prop-1-yl |
| A.287 | 3-(2'-cyanophenoxy)prop-1-yl |
| A.288 | 3-(3'-cyanophenoxy)prop-1-yl |
| A.289 | 3-(4'-cyanophenoxy)prop-1-yl |
| A.290 | 3-(2'-methylphenoxy)prop-1-yl |
| A.291 | 3-(3'-methylphenoxy)prop-1-yl |
| A.292 | 3-(4'-methylphenoxy)prop-1-yl |
| A.293 | 3-(2'-methoxyphenoxy)prop-1-yl |
| A.294 | 3-(3'-methoxyphenoxy)prop-1-yl |
| A.295 | 3-(4'-methoxyphenoxy)prop-1-yl |
| A.296 | 3-(2'-trifluoromethylphenoxy)prop-1-yl |
| A.297 | 3-(3'-trifluoromethylphenoxy)prop-1-yl |
| A.298 | 3-(4'-trifluoromethylphenoxy)prop-1-yl |
| A.299 | 4-phenoxybut-1-yl |
| A.300 | 2-phenyleth-1-yl |
| A.301 | 2-(2'-chlorophenyl)eth-1-yl |
| A.302 | 2-(3'-chlorophenyl)eth-1-yl |
| A.303 | 2-(4'-chlorophenyl)eth-1-yl |
| A.304 | 2-(3',5'-dichlorophenyl)eth-1-yl |
| A.305 | 2-(2'-cyanophenyl)eth-1-yl |
| A.306 | 2-(3'-cyanophenyl)eth-1-yl |
| A.307 | 2-(4'-cyanophenyl)eth-1-yl |
| A.308 | 2-(2'-methylphenyl)eth-1-yl |
| A.309 | 2-(3'-methylphenyl)eth-1-yl |
| A.310 | 2-(4'-methylphenyl)eth-1-yl |
| A.311 | 2-(2'-methoxyphenyl)eth-1-yl |
| A.312 | 2-(3'-methoxyphenyl)eth-1-yl |
| A.313 | 2-(4'-methoxyphenyl)eth-1-yl |
| A.314 | 2-(2'-trifluoromethylphenyl)eth-1-yl |
| A.315 | 2-(3'-trifluoromethylphenyl)eth-1-yl |
| A.316 | 2-(4'-trifluoromethylphenyl)eth-1-yl |
| A.317 | 3-phenylprop-1-yl |
| A.318 | 3-(2'-chlorophenyl)prop-1-yl |
| A.319 | 3-(3'-chlorophenyl)prop-1-yl |
| A.320 | 3-(4'-chlorophenyl)prop-1-yl |
| A.321 | 3-(2'-cyanophenyl)prop-1-yl |
| A.322 | 3-(3'-cyanophenyl)prop-1-yl |
| A.323 | 3-(4'-cyanophenyl)prop-1-yl |
| A.324 | 3-(2'-trifluoromethylphehyl)prop-1-yl |
| A.325 | 4-phenylbut-1-yl |
| A.326 | 4-(4'-chlorophenyl)but-1-yl |
| A.327 | 6-(4'-chlorophenyl)hex-1-yl |
| A.328 | 2-pyridylmethyl |
| A.329 | 3-pyridylmethyl |
| A.330 | 4-pyridylmethyl |
| A.331 | 4-chloropyridin-2-ylmethyl |
| A.332 | 5-chloropyridin-2-ylmethyl |
| A.333 | 6-chloropyridin-2-ylmethyl |
| A.334 | 5-chloropyridin-3-ylmethyl |
| A.335 | 6-chloropyridin-3-ylmethyl |
| A.336 | 2-chloropyridin-4-ylmethyl |
| A.337 | 2-pyrimidinylmethyl |
| A.338 | 4-chloropyrimidin-2-ylmethyl |
| A.339 | 5-chloropyrimidin-2-ylmethyl |
| A.340 | 2-chloropyrimidin-4-ylmethyl |
| A.341 | 6-chloropyrimidin-4-ylmethyl |
| A.342 | 2-chloropyrimidin-5-ylmethyl |
| A.343 | 4-pyridazinyl-methyl |
| A.344 | 2-pyrazinylmethyl |
| A.345 | 5-chloropyrazin-2-ylmethyl |
| A.346 | 6-chloropyrazin-2-ylmethyl |
| A.347 | 3-pyridazinylmethyl |
| A.348 | 6-chloropyridazin-3-ylmethyl |
| A.349 | 1,3,5-triazinylmethyl |
| A.350 | 2-furylmethyl |
| A.351 | 3-furylmethyl |
| A.352 | 4-bromofur-2-ylmethyl |
| A.353 | 5-chlorofur-2-ylmethyl |
| A.354 | 2-thienylmethyl |
| A.355 | 3-thienylmethyl |
| A.356 | 5-methylthien-3-ylmethyl |
| A.357 | 5-chlorothien-2-ylmethyl |
| A.358 | 2-chlorothien-4-ylmethyl |
| A.359 | 2-pyrrolylmethyl |
| A.360 | 3-pyrrolylmethyl |
| A.361 | 2-oxazolylmethyl |
| A.362 | 4-methyloxazol-2-ylmethyl |
| A.363 | 5-methyloxazol-2-ylmethyl |
| A.364 | 4-chlorooxazol-2-ylmethyl |
| A.365 | 5-chlorooxazol-2-ylmethyl |
| A.366 | 4-oxazolylmethyl |
| A.367 | 2-methyloxazol-4-ylmethyl |
| A.368 | 5-methyloxazol-4-ylmethyl |
| A.369 | 2-chlorooxazol-4-ylmethyl |
| A.370 | 5-chlorooxazol-4-ylmethyl |
| A.371 | 5-oxazolylmethyl |
| A.372 | 2-methyloxazol-5-ylmethyl |
| A.373 | 4-methyloxazol-5-ylmethyl |
| A.374 | 2-chlorooxazol-5-ylmethyl |
| A.375 | 4-chlorooxazol-5-ylmethyl |
| A.376 | 2-thiazolylmethyl |
| A.377 | 4-methylthiazol-2-ylmethyl |
| A.378 | 5-methylthiazol-2-ylmethyl |
| A.379 | 4-chlorothiazol-2-ylmethyl |
| A.380 | 5-chlorothiazol-2-ylmethyl |
| A.381 | 4-thiazolylmethyl |
| A.382 | 2-methylthiazol-4-ylmethyl |
| A.383 | 5-methylthiazol-4-ylmethyl |
| A.384 | 2-chlorothiazol-4-ylmethyl |
| A.385 | 5-chlorothiazol-4-ylmethyl |
| A.386 | 5-thiazolylmethyl |
| A.387 | 2-methylthiazol-5-ylmethyl |
| A.388 | 4-methylthiazol-5-ylmethyl |
| A.389 | 2-chlorothiazol-5-ylmethyl |
| A.390 | 4-chlorothiazol-5-ylmethyl |
| A.391 | 3-isoxazolylmethyl |
| A.392 | 4-methylisoxazol-3-ylmethyl |
| A.393 | 5-methylisoxazol-3-ylmethyl |
| A.394 | 4-chloroisoxazol-3-ylmethyl |
| A.395 | 5-chloroisoxazol-3-ylmethyl |
| A.396 | 4-isoxazolylmethyl |
| A.397 | 3-methylisoxazol-4-ylmethyl |
| A.398 | 5-methylisoxazol-4-ylmethyl |
| A.399 | 3-chloroisoxazol-4-ylmethyl |
| A.400 | 5-chloroisoxazol-4-ylmethyl |
| A.401 | 5-isoxazolylmethyl |
| A.402 | 3-methylisoxazol-5-ylmethyl |
| A.403 | 4-methylisoxazol-5-ylmethyl |
| A.404 | 3-chloroisoxazol-5-ylmethyl |
| A.405 | 4-chloroisoxazol-5-ylmethyl |
| A.406 | 3-isothiazolylmethyl |
| A.407 | 4-methylisothiazol-3-ylmethyl |
| A.408 | 5-methylisothiazol-3-ylmethyl |
| A.409 | 4-chloroisothiazol-3-ylmethyl |
| A.410 | 5-chloroisothiazol-3-ylmethyl |
| A.411 | 4-isothiazolylmethyl |
| A.412 | 3-methylisothiazol-4-ylmethyl |
| A.413 | 5-methylisothiazol-4-ylmethyl |

TABLE A-continued

| No. | R¹ |
|---|---|
| A.414 | 3-chloroisothiazol-4-ylmethyl |
| A.415 | 5-chloroisothiazol-4-ylmethyl |
| A.416 | 5-isothiazolylmethyl |
| A.417 | 3-methylisothiazol-5-ylmethyl |
| A.418 | 4-methylisothiazol-5-ylmethyl |
| A.419 | 3-chloroisothiazol-5-ylmethyl |
| A.420 | 4-chloroisothiazol-5-ylmethyl |
| A.421 | 4-imidazolylmethyl |
| A.422 | 1-phenylpyrazol-3-ylmethyl |
| A.423 | 1-methylimidaz-4-ylmethyl |
| A.424 | 1-phenyl-1,2,4-triazol-3-ylmethyl |
| A.425 | 1,2,4-oxadiazol-3-ylmethyl |
| A.426 | 5-chloro-1,2,4-oxadiazol-3-ylmethyl |
| A.427 | 5-methyl-1,2,4-oxadiazol-3-ylmethyl |
| A.428 | 5-trifluoromethyl-1,2,4-oxadiazol-3-ylmethyl |
| A.429 | 1,3,4-oxadiazol-2-ylmethyl |
| A.430 | 5-chloro-1,3,4-oxadiazol-2-ylmethyl |
| A.431 | 5-methyl-1,3,4-oxadiazol-2-ylmethyl |
| A.432 | 5-methoxy-1,3,4-oxadiazol-2-ylmethyl |
| A.433 | 1,2,4-thiadiazol-3-ylmethyl |
| A.434 | 5-chloro-1,2,4-thiadiazol-3-ylmethyl |
| A.435 | 5-methyl-1,2,4-thiadiazol-3-ylmethyl |
| A.436 | 1,3,4-thiadiazol-2-ylmethyl |
| A.437 | 5-chloro-1,3,4-thiadiazol-2-ylmethyl |
| A.438 | 5-methyl-1,3,4-thiadiazol-2-ylmethyl |
| A.439 | 5-cyano-1,3,4-thiadiazol-2-ylmethyl |
| A.440 | 2-(2'-pyridinyloxy)eth-1-yl |
| A.441 | 2-(3'-pyridinyloxy)eth-1-yl |
| A.442 | 2-(4'-pyridinyloxy)eth-1-yl |
| A.443 | 2-(2'-pyrimidinyloxy)eth-1-yl |
| A.444 | 2-(4'-pyrimidinyloxy)eth-1-yl |
| A.445 | 2-(5'-pyrimidinyloxy)eth-1-yl |
| A.446 | 2-(2'-pyrazinyloxy)eth-1-yl |
| A.447 | 2-(2'-pyridazinyloxy)eth-1-yl |
| A.448 | 2-(3'-pyridazinyloxy)eth-1-yl |
| A.449 | 2-(',3',5'-triazinyloxy)eth-1-yl |
| A.450 | 2-(5'-methylisoxazol-3'-yloxy)eth-1-yl |
| A.451 | 2-(5'-chloroisoxazol-3'-yloxy)eth-1-yl |
| A.452 | 2-(2'-methoxythiazol-4'-yloxy)eth-1-yl |
| A.453 | 2-(4'-chlorooxazol-2'-yloxy)eth-1-yl |
| A.454 | 2-(1'-phenyl-1'H-1',2',4'-triazol-3'-yloxy)eth-1-yl |
| A.455 | 2-(1'-phenylpyrazol-3'-yloxy)eth-1-yl |
| A.456 | C⁶H₅ |
| A.457 | 2-Cl—C₆H₄ |
| A.458 | 3-Cl—C₆H₄ |
| A.459 | 4-Cl—C₆H₄ |
| A.460 | 2,3-Cl₂—C₆H₃ |
| A.461 | 2,4-Cl₂—C₆H₃ |
| A.462 | 2,5-Cl₂—C₆H₃ |
| A.463 | 3,4-Cl₂—C₆H₃ |
| A.464 | 3,5-Cl₂—C₆H₃ |
| A.465 | 4-CN—C₆H₄ |
| A.466 | 2-NO₂—C₆H₄ |
| A.467 | 3-NO₂—C₆H₄ |
| A.468 | 4-NO₂—C₆H₄ |
| A.469 | 2,4-(NO₂)₂—C₆H₃ |
| A.470 | 2-CH₃—C₆H₄ |
| A.471 | 3-CH₃—C₆H₄ |
| A.472 | 4-CH₃—C₆H₄ |
| A.473 | 2,3-(CH₃)₂—C₆H₃ |
| A.474 | 2,4-(CH₃)₂—C₆H₃ |
| A.475 | 2,5-(CH₃)₂—C₆H₃ |
| A.476 | 2,6-(CH₃)₂—C₆H₃ |
| A.477 | 2-C₆H₅—C₆H₄ |
| A.478 | 3-C₆H₅—C₆H₄ |
| A.479 | 4-C₆H₅—C₆H₄ |
| A.480 | 3-OCH₃—C₆H₄ |
| A.481 | 4-OCH₃—C₆H₄ |
| A.482 | 3-acetyl-C₆H₄ |
| A.483 | 4-acetyl-C₆H₄ |
| A.484 | 3-methoxycarbonyl-C₆H₄ |
| A.485 | 4-methoxycarbonyl-C₆H₄ |
| A.486 | 3-CF₃—C₆H₄ |
| A.487 | 4-CF₃—C₆H₄ |
| A.488 | 2-naphthyl |
| A.489 | 6-chloropyrldazin-3-yl |
| A.490 | 5-chloropyrazin-2-yl |
| A.491 | quinolin-2-yl |
| A.492 | 2,5-dimethylpyrazin-3-yl |
| A.493 | pyrazin-2-yl |
| A.494 | 3-chloropyrid-2-yl |
| A.495 | 6-chloropyrid-2-yl |
| A.496 | 4-trifluoromethyl, 6-chloropyrid-2-yl |
| A.497 | 4-trifluoromethylpyrid-2-yl |
| A.498 | 6-trifluoromethylpyrid-2-yl |
| A.499 | 6-methoxypyrid-2-yl |
| A.500 | 5-chloropyrid-2-yl |
| A.501 | pyrid-2-yl |
| A.502 | benzothiazol-2-yl |
| A.503 | 7-chloroquinolin-4-yl |
| A.504 | 3-nitropyrid-2-yl |
| A.505 | pyrrol-3-yl |
| A.506 | pyrrol-2-yl |
| A.507 | 2,6-dioctylpyrid-4-yl |
| A.508 | 5-nitropyrid-2-yl |
| A.509 | pyrid-4-yl |
| A.510 | pyrid-3-yl |
| A.511 | pyrimidin-2-yl |
| A.512 | pyrimidin-4-yl |
| A.513 | quinazolin-4-yl |
| A.514 | 6-chloropyrimidin-4-yl |
| A.515 | 6-methoxypyrimidin-4-yl |
| A.516 | 2,5,6-trichloropyrimidin-4-yl |
| A.517 | 2,6-dimethylpyrimidin-4-yl |
| A.518 | 2-methyl, 6-chloropyrimidin-4-yl |
| A.519 | 2-methyl, 6-ethoxypyrimidin-4-yl |
| A.520 | 4,5,6-trichloropyrimidin-2-yl |
| A.521 | 4,6-dimethoxypyrimidin-2-yl |
| A.522 | 4,6-dimethylpyrimidin-2-yl |
| A.523 | 4,6-dichloropyrimidin-2-yl |
| A.524 | 4-methyl, 6-methoxypyrimidin-2-yl |
| A.525 | 4-chloro, 6-methoxypyrimidin-2-yl |
| A.526 | 6-chloroquinoxalin-2-yl |
| A.527 | 3,6-dichloro-1,2,4-triazin-5-yl |
| A.528 | 4-methoxy-1,3,5-triazin-2-yl |
| A.529 | 4-ethoxy-1,3,5-triazin-2-yl |
| A.530 | 4,6-dichloro-1,3,5-triazin-2-yl |
| A.531 | 4-ethoxyl, 6-chloro-1,3,5-triazin-2-yl |
| A.532 | isoxazol-3-yl |
| A.533 | thien-2-yl |
| A.534 | fur-2-yl |
| A.535 | thiatriazol-5-yl |
| A.536 | (E)-1-chloropropen-3-yl |
| A.537 | (E)-4-(4'-chlorophenyl)but-2-en-1-yl |
| A.538 | propyn-3-yl |
| A.539 | methylcarbonyl |
| A.540 | ethylcarbonyl |
| A.541 | n-propylcarbonyl |
| A.542 | i-propylcarbonyl |
| A.543 | n-butylcarbonyl |
| A.544 | s-butylcarbonyl |
| A.545 | i-butylcarbonyl |
| A.546 | t-butylcarbonyl |
| A.547 | n-pentylcarbonyl |
| A.548 | i-pentylcarbonyl |
| A.549 | neo-pentylcarbonyl |
| A.550 | n-hexylcarbonyl |
| A.551 | n-octylcarbonyl |
| A.552 | 1-propenylcarbonyl |
| A.553 | 2-penten-1-yl-carbonyl |
| A.554 | 2,5-heptadien-1-yl-carbonyl |
| A.555 | benzoyl |
| A.556 | 2-chlorobenzoyl |
| A.557 | 3-chlorobenzoyl |
| A.558 | 4-chlorobenzoyl |
| A.559 | 2-cyanobenzoyl |
| A.560 | 3-cyanobenzoyl |
| A.561 | 4-cyanobenzoyl |
| A.562 | 4-methoxybenzoyl |
| A.563 | 2-pyridylcarbonyl |
| A.564 | 3-pyridylcarbonyl |
| A.565 | 4-pyridylcarbonyl |
| A.566 | 2-pyrimidinylcarbonyl |
| A.567 | 2-oxazolylcarbonyl |

TABLE A-continued

| No. | R¹ |
|---|---|
| A.568 | 4-methylisoxazol-5-ylcarbonyl |
| A.569 | methylsulfonyl |
| A.570 | ethylsulfonyl |
| A.571 | n-propylsulfonyl |
| A.572 | i-propylsulfonyl |
| A.573 | n-butylsulfonyl |
| A.574 | t-butylsulfonyl |
| A.575 | n-pentylsulfonyl |
| A.576 | neo-pentylsulfonyl |
| A.577 | n-hexylsulfonyl |
| A.578 | n-octylsulfonyl |
| A.579 | phenylsulfonyl |
| A.580 | 2-chlorophenylsulfonyl |
| A.581 | 3-chlorophenylsulfonyl |
| A.582 | 4-chlorophenylsulfonyl |
| A.583 | 2-cyanophenylsulfonyl |
| A.584 | 3-cyanophenylsulfonyl |
| A.585 | 4-cyanophenylsulfonyl |
| A.586 | 2-pyridylsulfonyl |
| A.587 | 3-pyridylsulfonyl |
| A.588 | 4-pyridylsulfonyl |
| A.589 | 2-pyrimidinylsulfonyl |
| A.590 | 4-oxazolylsulfonyl |
| A.591 | 5-chlorothiazol-2-ylsulfonyl |
| A.592 | 2-t-C$^4$H$_9$—C$_6$H$_4$—CH$_2$ |
| A.593 | 3-t-C$_4$H$_9$—C$_6$H$_4$—CH$_2$ |
| A.594 | 4-t-C$_4$H$_9$—C$_6$H$_4$—CH$_2$ |
| A.595 | 2-(4'-chlorothiazol-2'-yloxy)eth-1-yl |
| A.596 | 2-(1'-methylpyrazol-4'-yloxy)eth-1-yl |
| A.597 | 4-Br—C$_6$H$_4$ |
| A.598 | 3,5-(CH$_3$)$_2$—C$_6$H$_3$ |
| A.599 | 4-C$_2$H$_5$—C$_6$H$_4$ |
| A.600 | 3-dimethylaminocarbonyl-C$_6$H$_4$ |
| A.601 | 4-dimethylaminocarbonyl-C$_6$H$_4$ |
| A.602 | 2-hydroxyprop-1-yl |
| A.603 | 6-hydroxy-2-methylpyrimidin-4-ylmethyl |
| A.604 | [6-OH,2-CH(CH$_3$)$_2$-pyrimidin-4-yl]-CH$_2$ |
| A.605 | [6-OH,2-CH(CH$_2$)$_2$-pyrimidin-4-yl]-CH$_2$ |
| A.606 | 5-(2'-furan)-pent-1-yl |
| A.607 | 5-(2'-N-methylpyrrol)-pent-1-yl |
| A.608 | [2-(4-Cl—C$_6$H$_4$)-oxazol-4-yl]-CH$_2$ |
| A.609 | 3-CF$_3$-pyridin-2-yl |
| A.610 | 5-CF$_3$-pyridin-2-yl |
| A.611 | 6-(2'-Thienyl)hex-1-yl |
| A.612 | H |

TABLE B

| Nr. | R² |
|---|---|
| B.31 | H |
| B.32 | CF$_3$ |
| B.33 | CH$_2$CH$_3$ |
| B.34 | C$_6$H$_5$ |
| B.35 | CH$_2$CH$_2$CH$_3$ |
| B.36 | CH(CH$_3$)$_2$ |
| B.37 | CH$_2$CH$_2$CH$_2$CH$_3$ |
| B.38 | CH(CH$_3$)CH$_2$CH$_3$ |
| B.39 | CH$_2$CH(CH$_3$)$_2$ |
| B.40 | C(CH$_3$)$_3$ |
| B.41 | CH$_2$CH$_2$CH$_2$CH$_2$CH$_3$ |
| B.42 | CH$_2$CH$_2$CH(CH$_3$)$_2$ |
| B.43 | CH$_2$C(CH$_3$)$_3$ |
| B.44 | cyclopropyl |
| B.45 | cyclopentyl |
| B.46 | CH$_2$CH$_2$CH$_2$CH$_2$CH$_2$CH$_3$ |
| B.47 | cyclohexyl |
| B.48 | Cl |
| B.49 | Br |
| B.50 | CN |
| B.51 | OCH$_3$ |
| B.52 | OCH$_2$CH$_3$ |
| B.53 | SCH$_3$ |
| B.54 | CH$_2$Cl |

TABLE B-continued

| Nr. | R² |
|---|---|
| B.55 | CH$^2$CH$_2$Cl |
| B.56 | CH$_2$CH$_2$CH$_2$Cl |
| B.57 | CH$_2$CH$_2$CH$_2$CH$_2$Cl |
| B.58 | CH$_2$Br |
| B.59 | CF$_2$CF$_3$ |
| B.60 | CH$_2$CF$_3$ |

The compounds I are suitable as fungicides.

The compounds I are distinguished by an outstanding activity against a broad spectrum of phytopathogenic fungi, in particular from the classes of the Ascomycetes, Phycomycetes and Basidiomycetes. Some of them act systemically and can be employed in crop protection as foliar- and soil-acting fungicides.

They are especially important for controlling a large number of fungi on a variety of crop plants such as wheat, rye, barley, oats, rice, corn, grass, cotton, soya beans, coffee, sugar cane, grape vines, fruit species, ornamentals and vegetable species such as cucumbers, beans and cucurbits, and on the seed of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grape vines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, vegetables and ornamentals, grape vines, *Cercospora arachidicola* on ground nuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grape vines, Alternaria species on vegetables and fruit.

Furthermore, the compounds I are suitable for controlling harmful fungi in the protection of materials (eg. wood, paper, fibers or tissues) and in the protection of stored products.

The compounds I are used by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose; in any case, it should guarantee fine and uniform distribution of the compound according to the invention. The formulations are prepared in a known manner, eg. by extending the active ingredient with solvents and/or carriers, if desired using emulsifiers and dispersants, it also being possible for other organic solvents to be used as auxiliary solvents if water is used as the diluent. Suitable auxiliaries are essentially the following: solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers, such as non-ionic and anionic emulsifiers (eg. polyoxyethylene fatty alcohol ethers, alkylsulfonates and arylsulfonates) and dispersants such as lignin-sulfite waste liquors and methylcellulose.

In general, the fungicidal compositions comprise from 0.1 to 95, preferably from 0.5 to 90, % by weight of active ingredient.

When used in crop protection, the rates of application are from 0.01 to 2.0 kg of active ingredient per ha, depending on the nature of the desired effect.

In general, amounts of from 0.001 to 0.1 g, preferably 0.01 to 0.05 g of active ingredients are required per kilogram of seed in the case of seed treatment.

When used in the protection of materials or stored products, the rate of application of active ingredient depends on the nature of the field of application and of the desired effect. Customary rates of application in the protection of materials are, for example, 0,001 g to 2 kg, preferably 0,005 g to 1 kg, of active ingredient per cubic meter of material treated.

In the use form as fungicides, the compositions according to the invention can also be present together with other active ingredients, eg. with herbicides, insecticides, growth regulators, fungicides, or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(l-methylheptyl)phenyl crotonate, 2-sec-butyl-4,6-dinitrophenyl 3,3-dimethylacrylate, 2-sec-butyl-4,6-dinitrophenyl isopropyl carbonate, di-isopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-N-(2,2,2-tri-chloroethyl)formamide, 1-(3,4-dichloroanilino)-1-formylamino-2,2,2-trichloroethane, 2,6-dimethyl-N-tridecyl-morpholine and its salts, 2,6-dimethyl-N-cyclododecylmorpholine and its salts, N-[3-(p-tert-butylphenyl)-2-methylpropyl]-cis-2,6-dimethyl-morph oline, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chloro-phenoxy)-3,3-dimethyl-1-(1H-1,2,4-triazol-1-yl)-2-bu tanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl-5-methyl-5-methoxymethyl]-1,3-oxazolidine-2,4-dione, 3-(3,5-dichlorophenyl)-1-isopropyl-carbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl) benzhydryl alcohol, N-(3-chloro-2,6-dinitro-4-trifluoromethylphenyl)-5-trifluoromethyl-3-chloro-2-aminopyridine, 1-((bis(4-fluorophenyl)methyl-silyl)methyl)-1H-1,2,4-triazole, strobilurins, such as methyl-E-methoxyimino-[α-(o-tolyloxy)-o-tolyl]acetate, methyl-E-2-{2-[6-(2-cyanophenoxy)pyrimidin-4-yloxy]phenyl}-3-methoxyacrylate, N-methyl-E-methoxyimino-[α-(2-phenoxyphenyl)]acetamide, N-methyl-E-methoxyimino-[α-(2,5-dimethyloxy)-o-tolyl] acetamide, anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline, phenylpyrroles, such as 4-(2,2-difluoro-1,3-benzodioxol-4-yl)-pyrrole-3-carbonitrile, cinnamamides, such as 3-(4-chlorophenyl)-3-(3,4-dimethoxyphenyl)acryloylmorpholine.

Furthermore, compounds of the formula I are suitable for efficiently controlling pests from the classes of the insects, arachnids and nematodes. They can be employed as pesticides in crop protection and in the hygiene, stored-product and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina), such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Der-*

*manyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the Nematodes, for example, root-knot nematodes, eg. *Meloidogyne hapla, Meloidogyne incognita, Meloidogyne javanica*, cyst-forming nematodes, eg. *Globodera rostochiensis, Heterodera avenae, Heterodera glycines, Heterodera schachtii, Heterodera trifolii*, stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading or granules by means of spraying, atomizing, dusting, spreading or pouring. The use forms depend entirely on the intended purposes; in any case, they should guarantee the finest possible distribution for the active ingredients according to the invention.

The concentrations of active ingredient in the ready-to-use preparations can be varied within substantial ranges.

In general, they are from 0.0001 to 10%, preferably from 0.01 to 1%.

The active ingredients can also be used successfully in the ultra-low-volume method (ULV), it being possible to apply formulations comprising over 95% by weight of active ingredient, or even the active ingredient without additives.

The rate of application of the active ingredient for controlling pests is from 0.1 to 2.0, preferably 0.2 to 1.0 kg/ha under field conditions.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivates, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (spraying powders, oil dispersions) by adding water. To prepare emulsions, pastes or oil dispersions, the substances, as such or dissolved in an oil or solvent, can be homogenized in water by means of wetting agent, tackifier, dispersant or emulsifier. Alternatively, it is possible to prepare concentrates composed of active ingredient, wetting agent, tackifier, dispersant or emulsifier and, if desired, solvent or oil, and these concentrates are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene, or of naphthalenesulfonic acid, with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, materials for spreading and dusts can be prepared by mixing or concomitantly grinding the active substances with a solid carrier.

In general, the formulations comprise from 0.01 to 95% by weight, preferably from 0.1 to 90% by weight of the active ingredient. The active ingredients are employed in a purity of from 90% to 100%, preferably 95% to 100% (according to NMR spectrum).

The following are examples of the formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which has been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients onto solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

Various types of oils, or herbicides, fungicides, other pesticides or bactericides may be admixed with the active ingredients, if desired also only immediately before use (tank mix). These active ingredients can be admixed with the agents according to the invention in a weight ratio of 1:10 to 10:1.

MODE(S) FOR CARRYING OUT THE INVENTION

The protocols shown in the synthesis examples below were used for obtaining other compounds I by altering the starting compounds appropriately.

EXAMPLE 1

Preparation of methyl α-pentyl-[2-(3'-benzyloxyiminomethyl-phenoxy)phenyl]-β-methoxyacrylate

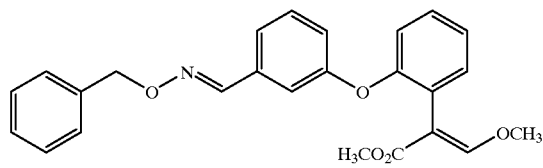

a) 3-hydroxybenzaldehyde O-benzyloxime 33.8 g of O-benzylhydroxylamine were added dropwise at approximately 25° C. to a mixture of 30.5 g of 3-hydroxybenzaldehyde and 300 ml of methanol (exothermic to approximately 35° C.). After approximately 12 hours, the reaction mixture was freed from volatile components under reduced pressure. The residue obtained was taken up in tert-butyl methyl ether. The organic phase was washed with water and subsequently dried. After removal of the solvent under reduced pressure, 60 g of the product were obtained as a pale solid; m.p.: 61–63° C.

b) methyl 3-bromophenylacetate

A solution of 83 g of 2-bromophenylacetic acid was added at approximately 25° C. to a solution of 45.5 g of acetyl chloride in 210 ml of methanol. After approximately 12 hours, the reaction mixture was freed from volatile components under reduced pressure. The residue obtained was taken up in tert-butyl methyl ether. The organic phase was washed with water and saturated NaHCO$_3$ solution and subsequently dried. After removal of the solvent under reduced pressure, 86.1 g of the product were obtained as a pale oil.

$^1$H NMR (CDCl$_3$): 3.70 (3H, s); 3.82 (2H, s); 7.1–7.6 (4H, m).

c) methyl 2-(3'-benzyloxyiminomethylphenoxy) phenylacetate

A mixture of 9.8 g of the ester of b), 14.6 g of the phenol of a), 8.9 g of potassium carbonate and 0.23 g of copper(I) chloride was stirred for 4 hours at 140° C. After cooling to room temperature (approximately 25° C.), the reaction mixture was mixed with water and tert-butyl methyl ether. The organic phase was washed with water and subsequently dried. After removal of the solvent and chromatographic purification (silica gel with cyclohexane/tert-butyl methyl ether 5:1 as the eluent), 2.7 g of the product were obtained as a pale resin.

$^1$H NMR (CDCl$_3$): 3.6 (3H, s); 3.7 (2H, s); 5.2 (2H, s); 6.8–7.5 (13H, m); 8.1 (1H, s).

d) methyl α-[2-(3'-benzyloxyiminomethylphenoxy)phenyl]-β-hydroxyacrylate

A mixture of 2.7 g of the product of c), 0.95 g of methyl formate and 8 ml of ether was added at approximately 25° C. to a suspension of 0.27 g of sodium hydride (97% pure) in 6 ml of ether. After approximately 12 hours at approximately 25° C., water was added to the reaction mixture, and the pH of the mixture was brought to approximately 3–4 using 10% strength HCl. The resulting mixture was extracted using ether. After washing, drying and removing the solvent under reduced pressure, the ether phase yielded 3.0 g of the product as a pale resin, which was further reacted without further purification.

$^1$H NMR (CDCl$_3$): 3.55 (3H, s); 5.17 (2H, s); 6.9–7.4 (14H, m); 8.07 (1H, s); 11.86 (1H, d).

e) methyl α-[2-(3'-benzyloxyiminomethyl-phenoxy) phenyl]-β-methoxyacrylate 1.0 g of potassium carbonate and 0.9 g of dimethyl sulfate were added at approximately 25° C. to a solution of 2.9 g of the product of d) in 10 ml of acetone. After approximately 12 hours, the reaction mixture was freed from volatile components under reduced pressure. The residue obtained was taken up in tert-butyl methyl ether. The organic phase was washed with water and saturated NH$_4$OH solution and subsequently dried. After removal of the solvent under reduced pressure, 3.0 g of the product were obtained in the form of the crude product, which was purified by chromatography on silica gel using cyclohexane/tert-butyl methyl ether 3:1 as the eluent. This gave 2.1 g of the product as a pale resin.

IR (cm$^{-1}$): 1710, 1636, 1570, 1489, 1444, 1290, 1253, 1215, 1129, 1103.

EXAMPLE 2

Preparation of methyl α-[2-(3'-benzyloxyiminomethyl-phenoxy)phenyl]-β-methylacrylate

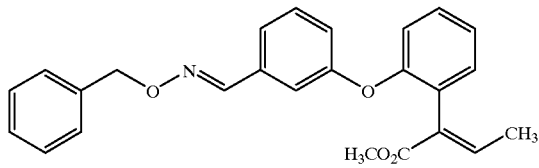

a) methyl 2-(3'-benzyloxyiminomethyl-phenoxy)phenylglyoxylate 1.46 g of potassium permanganate and 0.12 g of tetrahexylammonium hydrogen sulfate were added to a mixture of 1.94 g of the product of 1e), 10 ml of water and 10 ml of methylene chloride. After 1 hour, the reaction mixture was diluted with 50 ml of methylene chloride. The organic phase was separated off, and the aqueous phase was washed using a further 50 ml of methylene chloride. The combined organic phases were filtered through a frit packed with silica gel. Removal of the solvent gave the crude product, which was purified by chromatography on silica gel using cyclohexane/tert-butyl methyl ether 3:1 as the eluent. This gave 0.7 g of the product as a pale resin.

$^1$H NMR (CDCl$_3$): 3.7 (3H, s); 5.2 (2H, s); 6.8–8.0 (13H, m), 8.1 (1H, s).

b) methyl α-[2-(3'-benzyloxyiminomethyl-phenoxy)phenyl]-β-methylacrylate 0.18 g of potassium tert-butylate in 2.5 ml of tetrahydrofuran was added at 5° C. to a mixture of 0.6 g of the product of a), 0.57 g of ethyltriphenylphosphonium bromide and 5 ml of tetrahydrofuran. After 1 hour at 5° C. and 2 hours at 25° C., 50 ml of water were added to the reaction mixture, and the mixture was extracted twice using tert-butyl methyl ether. After washing, drying and removing the volatile components under reduced pressure, the organic phase yielded the crude product, which was purified by chromatography on silica gel using 1,2-dichloroethane/cyclohexane 1:2 as the eluent. This gave a total of 0.15 g of the product as a pale resin.

$^1$H NMR (CDCl$_3$): 1.74 (3H, d); 3.59 (3H, s); 5.17 (2H, s); 6.85–7.4 (14H, m); 8.05 (1H, s).

EXAMPLE 3

Preparation of methyl α-[2-(4'-methoxyiminoeth-1"-yl-phenoxy)phenyl]-β-methylacrylate (Table No. 15)

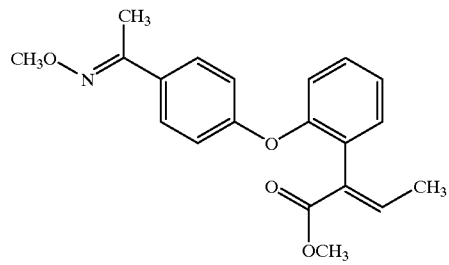

a) Methyl 2-(4'-methoxyiminoeth-1"-yl-phenoxy)phenylglyoxylate

A solution of 8.25 g of 4-hydroxyacetophenone O-methyloxime in 80 ml of dimethyl sulfoxide was added dropwise at approximately 25° C. to a suspension of 1.4 g of sodium hydride (95% pure) in 15 ml of dimethyl sulfoxide and the mixture was subsequently stirred for 30 minutes in an ultrasonic bath. A solution of 9.1 g of methyl 2-fluorophenylglyoxylate in 50 ml of dimethyl sulfoxide was added dropwise at approximately 25° C. After approximately 24 hours at approximately 25° C., the reaction mixture was treated with approximately 1.2 l of water. The resulting mixture was extracted using tert-butyl methyl ether. The combined organic phases were washed with water and subsequently dried. After removal of the solvent and chromatographic purification (silica gel and cyclohexane/tert-butyl methyl ether 5:1 as the eluent) 10.5 g of the product were obtained as a pale resin.

IR [cm$^{-1}$]: 1745, 1684, 1599, 1507, 1478, 1456, 1262, 1234, 1205, 1050.

b) Methyl α-[2-(4'-methoxyiminoeth-1"-yl-phenoxy)phenyl]-β-methylacrylate

A mixture of 3 g of the product of a), 3.4 g of ethyltriphenylphosphonium bromide and 25 ml of tetrahydrofuran was treated, at 5° C., with 1.1 g of potassium tert-butoxide in 13 ml of tetrahydrofuran. After 1 hour at 5° C. and 2 hours at 25° C., the reaction mixture was treated with approximately 250 ml of water and extracted three times using dichloromethane. Washing and drying the organic phase and removing the solvent gave the crude product which was purified by chromatography on silica gel using cyclohexane/tert-butyl methyl ether 8:1 as the solvent. This gave a total of 1.7 g of the product as a pale resin.

IR [cm$^{-1}$]: 1719, 1508, 1488, 1449, 1436, 1254, 1235, 1206, 1050, 892.

EXAMPLE 4

Preparation of methyl α-[2-(4'-methoxyiminoeth-1"-yl-phenoxy)phenyl]-β-methoxyacrylate (Table No. 14)

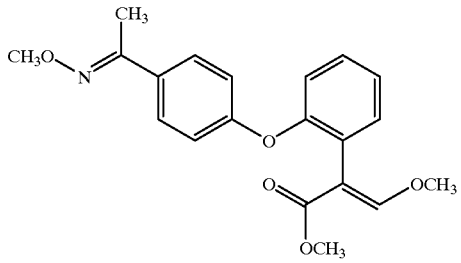

A mixture of 3 g of the product of 3a), 3.15 g of methoxymethyltriphenylphosphonium chloride and 25 ml of tetrahydrofuran was treated, at 5–10° C., with 1.1 g of potassium tert-butoxide in 13 ml of tetrahydrofuran. After 1 hour at 5° C. and approximately 12 hours at 25° C., the reaction mixture was treated with approximately 250 ml of water and extracted three times using dichloromethane. Washing and drying of the organic phase and removing the solvent gave the crude product which was purified by chromatography on silica gel using cyclohexane/tert-butyl methyl ether 5:1 as the eluent. This gave a total of 1.8 g of the product as a colorless solid.

m.p.: 88–90° C.

EXAMPLE 5

Preparation of methyl 2-(4'-methoxyiminoeth-1"-yl-phenoxy)phenylglyoxylate O-methyloxime (Table No. 13)

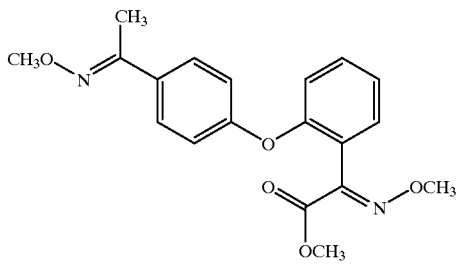

A mixture of 2.3 g of the product of 3a), 0.92 g of methoxyamine hydrochloride, 0.87 g of pyridine and 30 ml of methanol were heated for 2 hours at 60° C. After the mixture had cooled to approximately 25° C., it was concentrated. The residue which remained was taken up in tert-butyl methyl ether. Washing the organic phase with water, drying it and removing the solvent gave the crude product as an E/Z isomer mixture. To isomerize the mixture, it was dissolved in approximately 20 ml of methanol, and hydrogen chloride gas was passed in at approximately 5–10° C. to saturation point. The mixture was stirred for approximately 12 hours at approximately 25° C. After the solvent had been removed, the residue which remained was taken up in tert-butyl methyl ether. Washing the organic phase with water, drying it and removing the solvent gave the isomerized crude product which was purified by chromatography on silica gel using cyclohexane/tert-butyl methyl ether 5:1 as the eluent. In this manner, a total of 1.2 g of the product (E,E isomer) was obtained as a colorless solid.

m.p.: 89–91° C.

EXAMPLE 6

Preparation of N-methyl-2-(4'-methoxyiminoeth-1"-yl-phenoxy)phenylglyoxylamide O-methyloxime (Table No. 12)

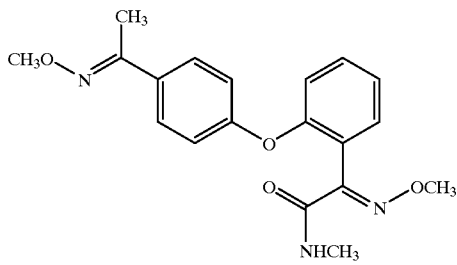

A mixture of 0.7 g of the product of Example 5, 1.55 g of methylamine (40% strength aqueous solution) and 15 ml of tetrahydrofuran was stirred for 2 hours at approximately 50° C. After the mixture had cooled, the solvent was removed under reduced pressure. The residue which remained was taken up in tert-butyl methyl ether. Washing the organic phase with water, drying it and removing the solvent gave 0.65 g of the product as a colorless solid.

m.p.: 105–107° C.

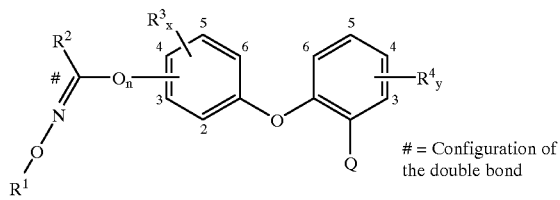

# = Configuration of the double bond

| No. | R¹ | R² | n | # | Pos | $R_x^3$ | $R_y^4$ | Q | m.p. [° C.]; IR [cm⁻¹]; ¹H—NMR [δ] |
|---|---|---|---|---|---|---|---|---|---|
| I.1 | C₆H₅—CH₂ | H | 0 | E | 3 | H | H | C(=CHOCH₃)COOCH₃ | (E) 1710, 1636, 1570, 1489, 1444, 1290, 1253, 1215, 1129, 1103. |

-continued

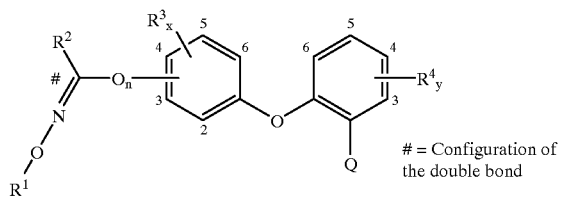

(I)

# = Configuration of the double bond

| No. | R¹ | R² | n | # | Pos | $R_x^3$ | $R_y^4$ | Q | | m.p. [° C.]; IR [cm⁻¹]; ¹H—NMR [δ] |
|---|---|---|---|---|---|---|---|---|---|---|
| I.2 | $C_6H_5$—$CH_2$ | H | 0 | E | 3 | H | H | C(=CHCH₃)COOCH₃ | (E) | 1,74(3H, d); 3,59(3H, s); 5,17 (2H, s); 6,85–7,4(14H, m); 8,05 (1H, s). |
| I.3 | CH₃ | CH₃ | 0 | E | 3 | H | H | C(=NOCH₃)CONHCH₃ | (E) | 1673, 1570, 1526, 1484, 1439, 1236, 1214, 1048, 980, 882. |
| I.4 | CH₃ | CF₃ | 0 | E | 3 | H | H | C(=NOCH₃)COOCH₃ | (E) | 1729, 1484, 1270, 1245, 1226, 1196, 1133, 1072, 1051, 1022. |
| I.5 | CH₃ | CF₃ | 0 | E | 3 | H | H | C(=NOCH₃)CONHCH₃ | (E) | 75–76 |
| I.6 | CH₃ | CF₃ | 0 | E | 3 | H | H | C(=NOCH₃)COOCH₃ | (Z) | 3,6(3H, s); 4,0(3H, s); 4,05 (3H, s); 6,9–7,9(8H, m). |
| I.7 | CH₃ | CH₃ | 0 | E | 3 | H | H | C(=NOCH₃)COOCH₃ | (E) | 1729, 1483, 1437, 1270, 1233, 1211, 1072, 1050, 1020, 882. |
| I.8 | CH₃ | CH₃ | 0 | E | 3 | H | H | C(=CHOCH₃)COOCH₃ | (E) | 1711, 1637, 1487, 1435, 1253, 1228, 1129, 1103, 1051, 882. |
| I.9 | CH₃ | CH₃ | 0 | E | 3 | H | H | C(=CHCH₃)COOCH₃ | (E) | 1719, 1569, 1487, 1448, 1434, 1254, 1227, 1200, 1050, 881. |
| I.10 | CH₃ | CH₃ | 0 | E | 3 | H | H | C(=NOCH₃)COOCH₃ | (Z) | 2,18(3H, s); 3,65(3H, s); 4,0 (3H, s); 4,05(3H, s); 6,8–7,85 (8H, m). |
| I.11 | CH₃ | CH₃ | 0 | E | 3 | H | H | C(=CHOCH₃)COOCH₃ | (Z) | 1722, 1634, 1485, 1434, 1272 1255, 1222, 1199, 1129, 1049. |
| I.12 | CH₃ | CH₃ | 0 | E | 4 | H | H | C(=NOCH₃)CONHCH₃ | (E) | 105–107 |
| I.13 | CH₃ | CH₃ | 0 | E | 4 | H | H | C(=NOCH₃)COOCH₃ | (E) | 89–91 |
| I.14 | CH₃ | CH₃ | 0 | E | 4 | H | H | C(=CHOCH₃)COOCH₃ | (E) | 88–90 |
| I.15 | CH₃ | CH₃ | 0 | E | 4 | H | H | C(=CHCH₃)COOCH₃ | (E) | 1719, 1508, 1488, 1449, 1436, 1254, 1235, 1206, 1050, 892. |
| I.16 | CH₃ | CH₃ | 0 | E | 4 | H | H | C(=NOCH₃)COOCH₃ | (Z) | 85–86 |
| I.17 | CH₃ | CH₃ | 0 | E | 4 | H | H | C(=CHOCH₃)COOCH₃ | (Z) | 1722, 1634, 1508, 1486, 1442, 1256, 1196, 1130, 1049. |
| I.18 | CH₃ | CF₃ | 0 | E | 3 | H | H | C(=CHOCH₃)COOCH₃ | (E) | 1712, 1638, 1486, 1437, 1251, 1193, 1155, 1130, 1052. |
| I.19 | CH₃ | CF₃ | 0 | E | 3 | H | H | C(=CHCH₃)COOCH₃ | (E) | 1719, 1486, 1436, 1253, 1216, 1195, 1156, 1133, 1050, 1028. |
| I.20 | C₂H₅ | CF₃ | 0 | E | 3 | H | H | C(=NOCH₃)CONHCH₃ | (E) | 82–83 |
| I.21 | C₂H₅ | CF₃ | 0 | E | 3 | H | H | C(=NOCH₃)COOCH₃ | (E) | 1730, 1484, 1270, 1245, 1226, 1195, 1132, 1072, 1049, 1023. |
| I.22 | C₂H₅ | CF₃ | 0 | E | 3 | H | H | C(=NOCH₃)COOCH₃ | (Z) | 1751, 1485, 1348, 1264, 1242, 1194, 1156, 1132, 1045. |
| I.23 | C₂H₅ | CF₃ | 0 | E | 3 | H | H | C(=CHCH₃)COOCH₃ | (E) | 1720, 1486, 1436, 1254, 1216, 1194, 1132, 1048, 1028. |
| I.24 | C₂H₅ | CF₃ | 0 | E | 3 | H | H | C(=CHOCH₃)COOCH₃ | (E) | 1712, 1638, 1486, 1250, 1193, 1155, 1130, 1103, 1051, 1027. |
| I.25 | C₂H₅ | CF₃ | 0 | E | 3 | H | H | C(=CHOCH₃)COOCH₃ | (Z) | 1723, 1635, 1485, 1436, 1245, 1194, 1155, 1129, 1049, 1027. |
| I.26 | CH₃ | CF₃ | 0 | E | 4 | H | H | C(=NOCH₃)CONHCH₃ | (E) | 120–122 |
| I.27 | CH₃ | CF₃ | 0 | E | 4 | H | H | C(=NOCH₃)COOCH₃ | (E) | 108–110 |
| I.28 | CH₃ | CF₃ | 0 | E | 4 | H | H | C(=NOCH₃)COOCH₃ | (Z) | 1751, 1506, 1265, 1233, 1206, 1191, 1172, 1133, 1050, 999. |
| I.29 | CH₃ | CF₃ | 0 | E | 4 | H | H | C(=CHCH₃)COOCH₃ | (E) | 67–68 |
| I.30 | CH₃ | CF₃ | 0 | E | 4 | H | H | C(=CHOCH₃)COOCH₃ | (E) | 77–79 |
| I.31 | CH₃ | C₆H₅ | 0 | E | 3 | H | H | C(=CHCH₃)COOCH₃ | (E) | 1719, 1483, 1445, 1434, 1254, 1231, 1052, 1032, 765, 699. |
| I.32 | CH₃ | C₆H₅ | 0 | E | 3 | H | H | C(=CHOCH₃)COOCH₃ | (E) | 1711, 1637, 1482, 1444, 1435, 1253, 1232, 1128, 1103, 1053. |
| I.33 | CH₃ | C₆H₅ | 0 | E | 3 | H | H | C(=NOCH₃)CONHCH₃ | (E) | 2937, 1676, 1574, 1526, 1482, 1445, 1238, 1051, 980, 699. |
| I.34 | CH₃ | C₆H₅ | 0 | E | 3 | H | H | C(=CHOCH₃)COOCH₃ | (Z) | 1721, 1634, 1483, 1434, 1271, 1255, 1228, 1197, 1129, 1051. |
| I.35 | CH₃ | * | 0 | E | 3 | * | H | C(=NOCH₃)CONHCH₃ | (E) | 130–131 |
| I.36 | CH₃ | * | 0 | E | 3 | * | H | C(=NOCH₃)COOCH₃ | (E) | 122–124 |
| I.37 | CH₃ | * | 0 | E | 3 | * | H | C(=CHCH₃)COOCH₃ | (E) | 1719, 1484, 1449, 1434, 1253, 1231, 1050, 1035, 867, 763. |
| I.38 | CH₃ | * | 0 | E | 3 | * | H | C(=CHOCH₃)COOCH₃ | (E) | 96–98 |

Nos. 35–38 are the following compounds:

-continued

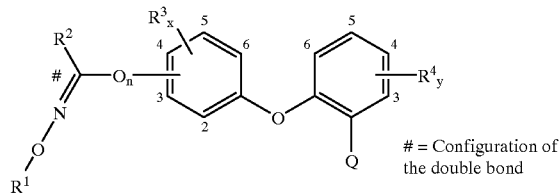

| No. | R¹ | R² | n | # | Pos | $R_x^3$ | $R_y^4$ | Q | m.p. [° C.]; IR [cm⁻¹]; ¹H—NMR [δ] |
|---|---|---|---|---|---|---|---|---|---|

Examples of the Activity Against Harmful Fungi

The fungicidal activity of the compounds of the general formula I was demonstrated by the following experiments:

The active ingredients were formulated as a 20% strength emulsion in a mixture of 70% by weight of cyclohexanone, 20% by weight of Nekanil® LN (Lutensol® AP6, wetting agent based on ethoxylated alkylphenols, with emulsifying and dispersant action) and 10% by weight of Emulphor® EL (Emulan® EL, emulsifier based on ethoxylated fatty alcohols) and diluted with water to give the desired concentration.

Activity against *Pyricularia oryzae* (Rice Blast Disease)

Rice seedlings (cultivar: "Tai Nong 67") were sprayed to run-off point with the preparation of active ingredient (rate of application: 63 ppm). After 24 hours, the plants were sprayed with an aqueous spore suspension of the fungus *Pyricularia oryzae* and kept for 6 days at 22–24° C. at a relative atmospheric humidity of 95–99%. Scoring was carried out visually.

The plants treated with compounds I.1, I.2, I.3, I.4, I.5, I.6, I.7, I.8, I.9, I.10, I.18, I.20, I.21, I.23, I.31 and I.33 showed a fungus attack of 15% and less, whereas the untreated (control) plants showed 75% fungus attack.

Action on *Erysiphe graminis* var. *tritici* (Powdery Mildew)

Leaves of wheat seedlings of the "Frühgold" variety were first treated with aqueous formulations of the active ingredients (appln. rate: 250 ppm). After about 24 hours the plants were dusted with spores of wheat mildew (*Erysiphe graminis* var. *tritici*). The plants treated in this manner were then incubated for 7 days at 20–22° C. and a relative humidity of 75–80%. The degree of fungus spread was then determined.

The plants treated with compounds I.1, I.2, I.3, I.4, I.5, I.6, I.7, I.8, I.9, I.10, I.12, I.13, I.14, I.15, I.16, I.17, I.18, I.19, I.20, I.21, I.22, I.23, I.24, I.25, I.26, I.27, I.30, I.31, I.32, I.33, I.34, I.35, I.37 and I.38 showed a fungus attack of 15% and less, whereas the untreated (control) plants showed 75% fungus attack.

Action on *Plasmopara viticola* (Downy Mildew)

Potted vines of the "Müller Thurgau" variety were sprayed to runoff with formulations of the active ingredients (appln. rate: 250 ppm). After 8 days the plants were sprayed with a zoospore suspension of the fungus *Plasmopara viticola*, and kept for 5 days at 20–30° C. and a high relative humidity. The plants were subsequently kept at a high relative humidity for 16 hours before being assessed. Assessment was visual.

The plants treated with compounds 1.3, I.4, I.5, I.6, I.7, I.8, I.9, I.10, I.11, I.18, I.19, I.20, I.22, I.24, I.27, 1.31, I.32, I.33, I.34, I.35, I.36, I.37 and I.38 showed a fungus attack of 15% and less, whereas the untreated (control) plants showed 80% fungus attack.

Examples of the Activity Against Animal Pests

The activity of the compounds of the general formula I against animal pests was demonstrated by the following experiments:

The active ingredients were formulated a. as a 0.1% strength solution in acetone or b. as a 10% strength emulsion in a mixture of 70% by weight of cyclohexanone, 20% by weight of Nekanil® LN (Lutensol® AP6, wetting agent based on ethoxylated alkylphenols, with emulsifying and dispersant action) and 10% by weight of Emulphor® EL (Emulan® EL, emulsifier based on ethoxylated fatty alcohols)

and diluted to give the desired concentration, either with acetone in the case of a. or water in the case of b.

After the experiments had ended, the lowest concentration was determined in each case where the compounds still caused an 80 to 100% inhibition or mortality in comparison with untreated controls (limit or minimum concentration).

*Nephotettix cincticeps* (Rice Leafhopper), Contact Action

Circular filter papers were treated with aqueous active ingredient formulations; 5 adult leaf hoppers were then placed on each filter paper. The kill rate was determined after 24 hours.

In this test compounds I.4, I.19, I.20 and I.21 showed an action threshold of 0.2 mg.

We claim:

1. A diphenyl ether of the formula I,

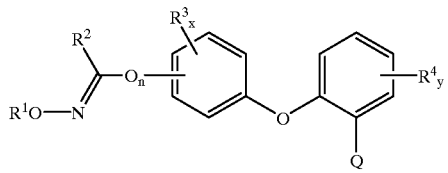

(I)

or a salt or N-oxide thereof where the substituents and the indices have the following meanings:

Q is $C(CONH_2)=CHOCH_3$, $C(CO_2CH_3)=NOCH_3$, $C(CONHCH_3)=NOCH_3$ or $N(OCH_3)-CO_2CH_3$;

n is 0 or 1;

$R^1$ is hydrogen or one of the following groups: unsubstituted or substituted alkyl, alkenyl, alkynyl, cycloalkyl, heterocyclyl, aryl or heteroaryl;

$R^2$ is hydrogen or one of the following groups: unsubstituted or substituted alkyl, alkenyl, alkynyl, cycloalkyl, heterocyclyl, aryl or heteroaryl, it being possible for these groups to be linked to the skeleton directly (via a carbon atom) or via an oxygen, sulfur or nitrogen atom;

x is 0, 1 or 2, it being possible for the radicals $R^3$ to be different if x is 2;

$R^3$ is cyano, nitro, halogen or one of the following groups: unsubstituted or substituted alkyl, alkenyl, alkynyl, cycloalkyl, heterocyclyl, aryl or heteroaryl, it being possible for these groups to be linked to the skeleton directly (via a carbon atom) or via an oxygen, sulfur or nitrogen atom or $R^2$ and a substituent $R^3$ which is adjacent to the group $O_n-C(R^2)=NOR^1$ is $C_2-C_3$-alkylene which can be interrupted by an oxygen or sulfur atom or can be linked to the phenyl ring via an oxygen or sulfur atom;

y is 0, 1, 2 or 3, it being possible for the radicals $R^4$ to be different if y is 2 or 3;

$R^4$ is cyano, halogen, $C_1-C_4$-alkyl, $C_1-C_4$-haloalkyl or $C_1-C_4$-alkoxy.

2. A process for the preparation of a compound I as claimed in claim 1 where n is 0, which comprises converting a phenol of the formula IIa

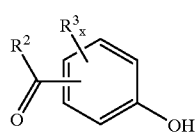

(IIa)

with a halobenzene of the formula IIIa

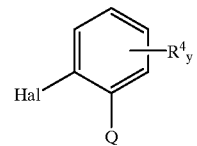

(IIIa)

where Hal is a halogen atom in an inert solvent to give the corresponding ether of the formula IVa

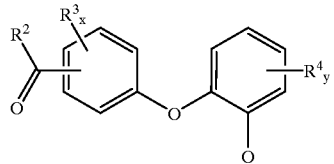

(IVa)

and subsequently reacting IVa with an O-substituted hydroxylamine ($R^1-O-NH_2$) or with a salt thereof to give I.

3. A process for the preparation of a compound I as claimed in claim 1 where n is 0, which comprises converting a phenol of the formula IIa

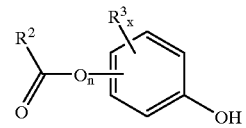

(IIa)

with an O-substituted hydroxylamine ($R^1-O-NH_2$) or with a salt thereof to give the corresponding compound of the formula IIb

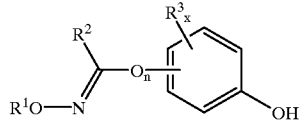

(IIb)

and subsequently reacting IIb with a fluorobenzene of the formula IIIa

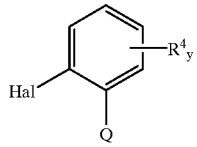

(IIIa)

where Hal is fluorine in an inert solvent to give I.

4. A process for the preparation of a compound IVa as set forth in claim 2 where n is 0, which comprises reacting an ether of the formula IVb

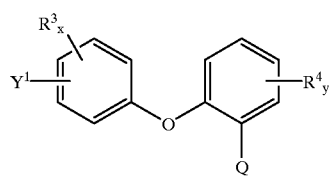
(IVb)

where Y¹ is a halogen atom either
a) with an activated carboxylic acid of the formula Va

(Va)

where $Y^2$ is a halogen atom, an amide or an ester radical, or with a corresponding cyanide $R^2$—C≡N, in an inert solvent in the presence of an organometallic base, or
b) with an organotin compound of the formula VI

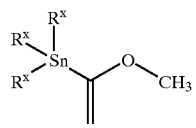
(VI)

where the radicals $R^x$ independently of one another are alkyl, in an inert solvent.

5. A process for the preparation of a compound I as claimed in claim 1 where n is 1, which comprises converting a diphenyl ether of the formula IVc

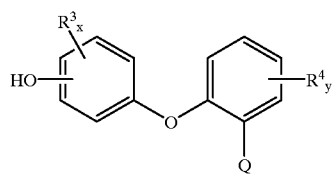
(IVc)

with a cyanide $R^2$—C≡N in an inert solvent in the presence of hydrochloric acid to give the chlorohydroxamate VIIc

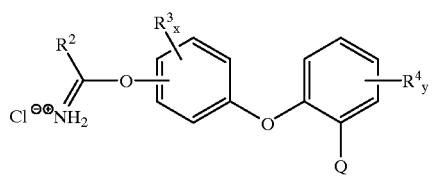
(VIIc)

and subsequently reacting VIIc with an O-substituted hydroxylamine ($R^1$—ONH$_2$) or with a salt thereof to give I.

6. A process for the preparation of a compound I as claimed in claim 1 where n is 0 and Q is C(CO$_2$CH$_3$)=NOCH$_3$, which comprises converting a phenol of the formula IIa

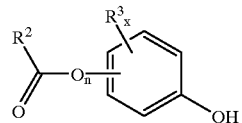
(IIa)

with a halobenzene of the formula IIIb

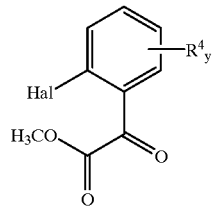
(IIIb)

where Hal is a halogen atom in an inert solvent to give the corresponding ether of the formula VIIa

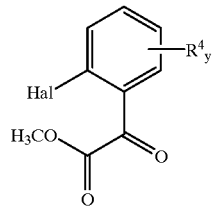
(VIIa)

subsequently reacting VIIa with an O-substituted hydroxylamine ($R^1$—ONH$_2$) or with a salt thereof to give VIIb (VIIb)

and reacting VIIb with O-methylhydroxylamine (CH$_3$—ONH$_2$) or with a salt thereof.

7. A process for the preparation of a compound VIIb as set forth in claim 6, which comprises reacting a compound of the formula IIb (IIb)

with a halobenzene of the formula IIIb

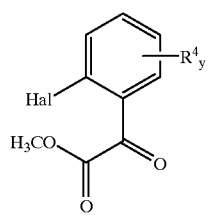

where Hal is a halogen atom.

8. A process for the preparation of a compound I as claimed in claim 1 where n is 0 and Q is C(CONHCH$_3$)=NOCH$_3$, which comprises first converting a compound of the formula IIb

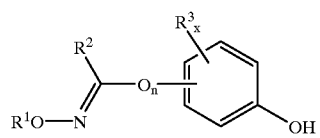

with a halobenzene of the formula IIIc

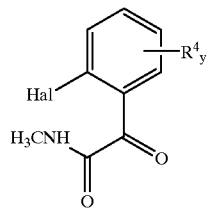

where Hal is a halogen atom in an inert solvent to give the corresponding ether of the formula VIId

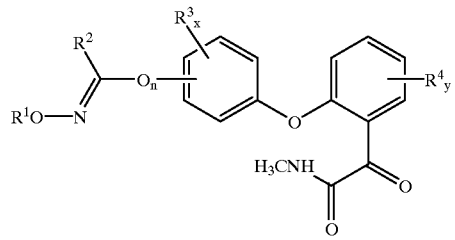

and reacting VIId with O-methylhydroxylamine (CH$_3$O—NH$_2$) or the salt thereof.

9. A process for the preparation of a compound I as claimed in claim 1 where Q is C(CO$_2$CH$_3$)=CHOCH$_3$, which comprises converting a phenylacetic acid of the formula VIIIa

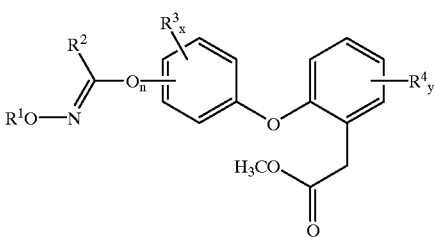

in an inert solvent in a manner known per se to give the corresponding β-hydroxyacrylate VIIIb

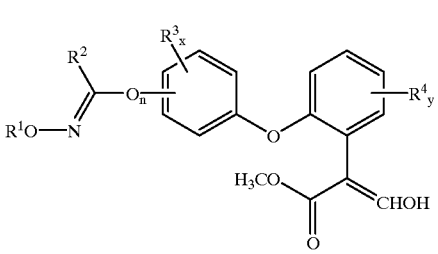

and reacting VIIIb with a methylating reagent to give I.

10. An intermediate of the general formula IV'

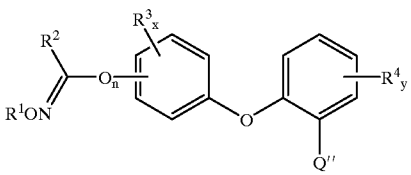

where R$^1$, R$^2$, R$^3$, R$^4$, n, x and y have the meanings given in claim 1 and Q'' is one of the following groups: CH$_2$—CO$_2$CH$_3$ or C(O)—CO$_2$CH$_3$.

11. A composition which is suitable for controlling pests or harmful fungi, comprising a solid or liquid carrier and a compound of the general formula I as claimed in claim 1.

12. A method of controlling harmful fungi, which comprises treating the fungi, or the materials, plants, the soil or seeds to be protected against fungal infection, with an effective amount of a compound of the general formula I as claimed in claim 1.

13. A method of controlling pests, which comprises treating the pests, or the materials, plants, the soil or seeds to be protected against them, with an effective amount of a compound of the general formula I as claimed in claim 1.

14. The diphenyl ether defined in claim 1, wherein R$^1$ is hydrogen; C$_1$–C$_6$-alkyl; C$_3$–C$_6$-alkenyl; C$_3$–C$_6$-alkynyl; C$_1$–C$_6$-haloalkyl; C$_3$–C$_6$-haloalkenyl; aryl-C$_1$–C$_2$-alkyl, wherein the aryl radical is unsubstituted or substituted; C$_3$–C$_6$-cycloalkyl-C$_1$–C$_2$-alkyl, wherein the cycloalkyl radical is unsubstituted or substituted; or hetaryl-C$_1$–C$_2$-alkyl, wherein the hetaryl radical is unsubstituted or substituted.

15. The diphenyl ether defined in claim 1, wherein R$^2$ is C$_1$–C$_6$-alkyl; C$_2$–C$_6$-alkenyl; C$_2$–C$_6$-alkynyl; C$_3$–C$_6$-cycloalkyl; aryl; or hetaryl.

16. The diphenyl ether defined in claim 1, wherein x is 0 or 1.

17. The diphenyl ether defined in claim 1, wherein $R^3$ is halogen, $C_1$–$C_2$-alkyl, $C_1$–$C_2$-alkoxy, cyano or nitro.

18. The diphenyl ether defined in claim 1, wherein y is 0 or 1.

19. The diphenyl ether defined in claim 1, wherein $R^4$ is cyano, halogen, $C_1$–$C_3$-alkyl, $C_1$–$C_2$-haloalkyl or $C_1$–$C_3$-alkoxy.

20. The diphenyl ether defined in claim 1, wherein $R^1$ is methyl, ethyl or benzyl;

$R^2$ is hydrogen, methyl, trifluoromethyl or phenyl, or together with $R^3$ forms —$CH_2CH_2CH_2$—, where said $R^3$ is bonded to the phenyl ring adjacent to the group $O_n$—$C(R^2)$=$NOR^1$;

x is 0 or 1, and

Y is 0.

* * * * *